United States Patent
Wacker et al.

(10) Patent No.: US 7,126,010 B2
(45) Date of Patent: Oct. 24, 2006

(54) BENZYLCYCLOALKYL AMINES AS MODULATORS OF CHEMOKINE RECEPTOR ACTIVITY

(75) Inventors: Dean A Wacker, Chadds Ford, PA (US); John V Duncia, Hockessin, DE (US); Joseph B Santella, III., Springfield, PA (US); Daniel S Gardner, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 11/040,585

(22) Filed: Jan. 21, 2005

(65) Prior Publication Data
US 2005/0124671 A1    Jun. 9, 2005

Related U.S. Application Data

(62) Division of application No. 10/613,841, filed on Jul. 3, 2003, now Pat. No. 6,864,380, which is a division of application No. 09/687,192, filed on Oct. 13, 2000, now Pat. No. 6,608,227.

(60) Provisional application No. 60/159,899, filed on Oct. 15, 1999.

(51) Int. Cl.
| | |
|---|---|
| C07D 207/04 | (2006.01) |
| C07D 211/06 | (2006.01) |
| A61K 31/40 | (2006.01) |
| A61K 31/445 | (2006.01) |
| C07D 307/04 | (2006.01) |

(52) U.S. Cl. ............... 548/557; 546/224; 514/329; 514/426

(58) Field of Classification Search ........ 548/557, 548/527; 514/426, 329; 546/224
See application file for complete search history.

(56) References Cited

U.S. PATENT DOCUMENTS

| | | |
|---|---|---|
| 5,668,151 A | 9/1997 | Poindexter et al. |
| 5,783,593 A | 7/1998 | Baker et al. |
| 6,608,227 B1 * | 8/2003 | Wacker et al. ............ 564/50 |
| 6,864,380 B1 * | 3/2005 | Wacker et al. ............ 549/480 |
| 6,939,890 B1 * | 9/2005 | Harper et al. ............ 514/419 |

FOREIGN PATENT DOCUMENTS

| | | |
|---|---|---|
| WO | 93/06108 | 4/1993 |
| WO | 94/20062 | 9/1994 |
| WO | 95/12572 | 5/1995 |
| WO | 95/13069 | 5/1995 |
| WO | 97/20823 | 6/1997 |
| WO | 98/25604 | 6/1998 |
| WO | 99/17777 | 4/1999 |
| WO | 92/27939 | 6/1999 |
| WO | 00/35449 | 6/2000 |
| WO | 00/35451 | 6/2000 |
| WO | 00/35452 | 6/2000 |
| WO | 00/35453 | 6/2000 |
| WO | 00/35454 | 6/2000 |
| WO | 00/35876 | 6/2000 |
| WO | 00/35877 | 6/2000 |

\* cited by examiner

*Primary Examiner*—Shailendra Kumar
(74) *Attorney, Agent, or Firm*—Mary K. VanAtten

(57) ABSTRACT

The present application describes modulators of CCR3 of formula (I):

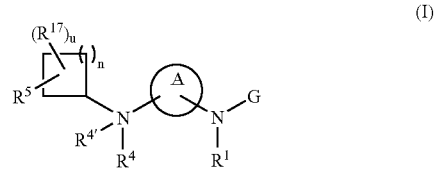

or pharmaceutically acceptable salt forms thereof, useful for the prevention of inflammatory diseases such as asthma and other allergic diseases.

16 Claims, No Drawings

BENZYLCYCLOALKYL AMINES AS MODULATORS OF CHEMOKINE RECEPTOR ACTIVITY

CROSS-REFERENCE TO RELATED APPLICATIONS

This application is a divisional of U.S. application Ser. No. 10/613,841, filed Jul. 3, 2003, now U.S. Pat. No. 6,864,380 which is a divisional of U.S. application Ser. No. 09/687,192, filed Oct. 13, 2000, now U.S. Pat. No. 6,608,227 which claims priority to Provisional Application No. 60/159,899, filed Oct. 15, 1999.

FIELD OF THE INVENTION

This invention relates generally to modulators of chemokine receptor activity, pharmaceutical compositions containing the same, and methods of using the same as agents for treatment and prevention of inflammatory diseases such as allergic diseases and asthma, as well as autoimmune pathologies such as rheumatoid arthritis and atherosclerosis.

BACKGROUND OF THE INVENTION

Chemokines are chemotactic cytokines, of molecular weight 6–15 kDa, that are released by a wide variety of cells to attract and activate, among other cell types, macrophages, T and B lymphocytes, eosinophils, basophils and neutrophils (reviewed in Luster, New Eng. J Med., 338, 436–445 (1998) and Rollins, Blood, 90, 909–928 (1997)). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seven-transmembrane-domain proteins (reviewed in Horuk, Trends Pharm. Sci., 15, 159–165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR-1 (or "CKR-1" or "CC-CKR-1") [MIP-1α, MCP-3, MCP-4, RANTES] (Ben-Barruch, et al., Cell, 72, 415–425 (1993), Luster, New Eng. J. Med., 338, 436–445 (1998)); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo et al., Proc. Natl. Acad. Sci. USA, 91, 2752–2756 (1994), Luster, New Eng. J. Med., 338, 436–445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491–16494 (1995), Luster, New Eng. J. Med., 338, 436–445 (1998)); CCR-4 (or "CKR-4" or "CC-CKR-4") [TARC, MIP-1α, RANTES, MCP-1] (Power et al., J. Biol. Chem., 270, 19495–19500 (1995), Luster, New Eng. J. Med., 338, 436–445 (1998)); CCR-5 (or "CKR-5" OR "CC-CKR-5") [MIP-1α, RANTES, MIP-1β] (Sanson, et al., Biochemistry, 35, 3362–3367 (1996)); CCR-6 (or "CKR-6" or "CC-CKR-6") [LARC] (Baba et al., J. Biol. Chem., 272, 14893–14898 (1997)); CCR-7 (or "CKR-7" or "CC-CKR-7") [ELC] (Yoshie et al., J. Leukoc. Biol. 62, 634–644 (1997)); CCR-8 (or "CKR-8" or "CC-CKR-8") [I-309, TARC, MIP-1β] (Napolitano et al., J. Immunol., 157, 2759–2763 (1996), Bernardini et al., Eur. J. Immunol., 28, 582–588 (1998)); and CCR-10 (or "CKR-10" or "CC-CKR-10") [MCP-1, MCP-3] (Bonini et al, DNA and Cell Biol., 16, 1249–1256 (1997)).

In addition to the mammalian chemokine receptors, mammalian cytomegaloviruses, herpesviruses and poxviruses have been shown to express, in infected cells, proteins with the binding properties of chemokine receptors (reviewed by Wells and Schwartz, Curr. Opin. Biotech., 8, 741–748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR3 expressing cells by HIV or in preventing the manipulation of immune cellular responses by viruses such as cytomegaloviruses.

A substantial body of art has accumulated over the past several decades with respect to substituted piperidines and pyrrolidines. These compounds have implicated in the treatment of a variety of disorders.

WO 98/25604 describes spiro-substituted azacycles which are useful as modulators of chemokine receptors:

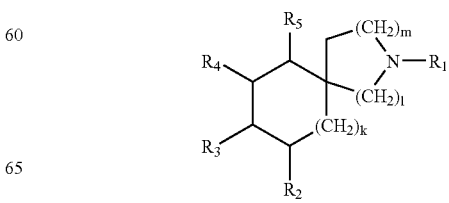

wherein $R_1$ is $C_{1-6}$ alkyl, optionally substituted with functional groups such as —$NR^6CONHR^7$, wherein $R^6$ and $R^7$ may be phenyl further substituted with hydroxy, alkyl, cyano, halo and haloalkyl. Such spiro compounds are not considered part of the present invention.

WO 95/13069 is directed to certain piperidine, pyrrolidine, and hexahydro-1H-azepine compounds of general formula:

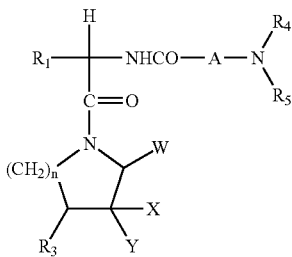

wherein A may be substituted alkyl or Z-substituted alkyl, with $Z=NR_{6a}$ or O. Compounds of this type are claimed to promote the release of growth hormone in humans and animals.

WO 93/06108 discloses pyrrolobenzoxazine derivatives as 5-hydroxytryptamine (5-HT) agonists and antagonists:

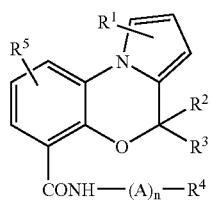

wherein A is lower alkylene and $R^4$ may be phenyl optionally substituted with halogen.

U.S. Pat. No. 5,668,151 discloses Neuropeptide Y (NPY) antagonists comprising 1,4-dihydropyridines with a piperidinyl or tetrahydropyridinyl-containing moiety attached to the 3-position of the 4-phenyl ring:

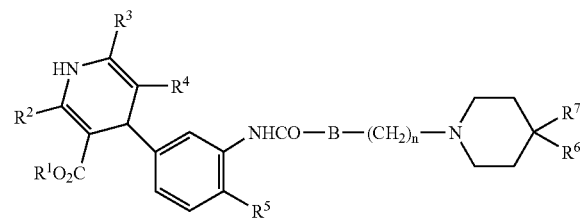

wherein B may be NH, $NR^1$, O, or a bond, and $R^7$ may be substituted phenyl, benzyl, phenethyl and the like.

Patent publication EP 0 903 349 A2 discloses CCR-3 receptor antagonists comprising cyclic amines of the following structure:

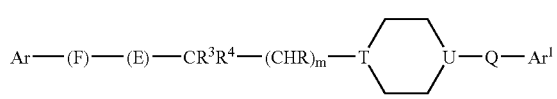

wherein T and U may be both nitrogen or one of T and U is nitrogen and the other is carbon and E may be —$NR^6CONR^5$— and others.

These reference compounds are readily distinguished structurally by either the nature of the urea functionality, the attachment chain, or the possible substitution of the present invention. The prior art does not disclose nor suggest the unique combination of structural fragments which embody these novel piperidines and pyrrolidines as having activity toward the chemokine receptors.

SUMMARY OF THE INVENTION

Accordingly, one object of the present invention is to provide novel agonists or antagonists of CCR-3, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating inflammatory disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

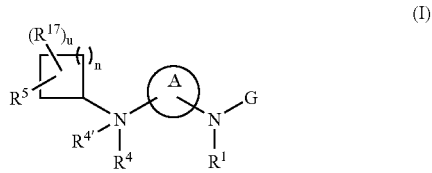

or stereoisomers or pharmaceutically acceptable salts thereof, wherein A, G, $R^1$, $R^4$, $R^{4'}$, $R^5$, $R^{17}$, n and u are defined below, are effective modulators of chemokine activity.

DETAILED DESCRIPTION OF THE EMBODIMENTS

[1] Thus, in a first embodiment, the present invention provides novel compounds of formula (I):

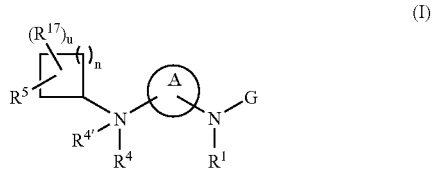

or stereoisomers or pharmaceutically acceptable salts thereof, wherein:

A is selected from

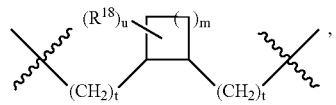

-continued

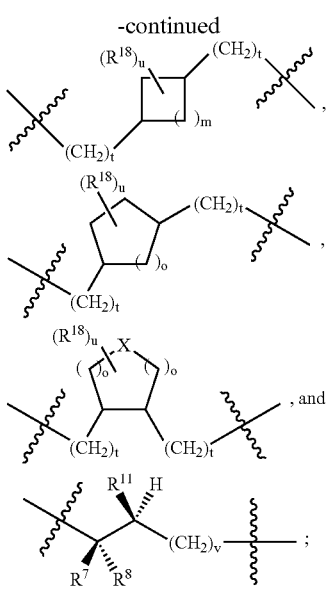

G is selected from —C(O)R$^3$, —C(O)NR$^2$R$^3$, —C(O)OR$^3$, —SO$_2$NR$^2$R$^3$, —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, C(=C(CN)$_2$)NR$^2$R$^3$,

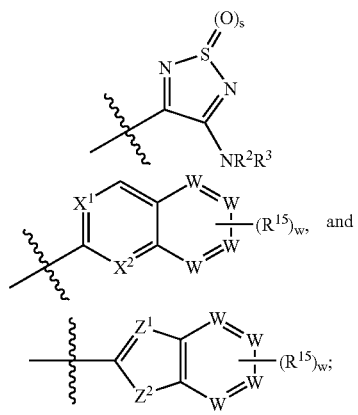

W, at each occurrence, is independently selected from C or N, provided at least two of W are C;

X is selected from O, S, and NR$^{19}$;

X$^1$ and X$^2$ are independently selected from C and N;

Z$^1$ is selected from C and N;

Z$^2$ is selected from NR$^{1a}$, O, S and C;

R$^1$ and R$^2$ are independently selected from H, C$_{1-8}$ alkyl, C$_{3-8}$ alkenyl, C$_{3-8}$ alkynyl, and a (CH$_2$)$_r$—C$_{3-10}$ carbocyclic residue substituted with 0–5 R$^a$;

R$^{1a}$ is independently selected from H, C$_{1-6}$ alkyl, (CH$_2$)$_r$C$_{3-6}$ cycloalkyl, and a (CH$_2$)$_r$—C$_{3-10}$ carbocyclic residue substituted with 0–5 R$^a$;

R$^a$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^b$R$^b$, (CH$_2$)$_r$OH, (CH$_2$)$_r$OR$^c$, (CH$_2$)$_r$SH, (CH$_2$)$_r$SR$^c$, (CH$_2$)$_r$C(O)R$^b$, (CH$_2$)$_r$C(O)NR$^b$R$^b$, (CH$_2$)$_r$NR$^b$C(O)R$^b$, (CH$_2$)$_r$C(O)OR$^b$, (CH$_2$)$_r$OC(O)R$^c$, (CH$_2$)$_r$CH(=NR$^b$)NR$^b$R$^b$, (CH$_2$)$_r$NHC(=NR$^b$)NR$^b$R$^b$, (CH$_2$)$_r$S(O)$_p$R$^c$, (CH$_2$)$_r$S(O)$_2$NR$^b$R$^b$, (CH$_2$)$_r$NR$^b$S(O)$_2$R$^c$, and (CH$_2$)$_r$phenyl;

R$^b$, at each occurrence, is selected from H, C$_{1-6}$ alkyl, C$_{3-6}$ cycloalkyl, and phenyl;

R$^c$, at each occurrence, is selected from C$_{1-6}$ alkyl, C$_{3-6}$ cycloalkyl, and phenyl;

alternatively, R$^2$ and R$^3$ join to form a 5, 6, or 7-membered ring substituted with 0–3 R$^a$;

R$^3$ is selected from a (CR$^{3'}$R$^{3''}$)$_r$—C$_{3-10}$ carbocyclic residue substituted with 0–5 R$^{15}$ and a (CR$^{3'}$R$^{3''}$)$_r$-5–10 membered heterocyclic system containing 1–4 heteroatoms selected from N, O, and S, substituted with 0–3 R$^{15}$;

R$^{3'}$ and R$^{3''}$, at each occurrence, are selected from H, C$_{1-6}$ alkyl, (CH$_2$)$_r$C$_{3-6}$ cycloalkyl, and phenyl;

R$^4$ is hydrogen, C$_{1-8}$ alkyl, C$_{2-8}$ alkenyl, C$_{2-8}$ alkynyl, (CH$_2$)$_r$C$_{3-6}$ cycloalkyl, and a (CH$_2$)$_r$—C$_{3-10}$ carbocyclic residue substituted with 0–5 R$^a$;

alternatively, R$^4$ joins with R$^8$ or R$^{11}$ to form a pyrrolidine or piperidine ring system substituted with 0–3 R$^{4d}$;

R$^{4'}$ is absent, taken with the nitrogen to which it is attached to form an N-oxide, or selected from C$_{1-8}$ alkyl, C$_{2-8}$ alkenyl, C$_{3-8}$ alkynyl, (CH$_2$)$_r$C$_{3-6}$ cycloalkyl, (CH$_2$)$_q$C(O)R$^{4b}$, (CH$_2$)$_q$C(O)NR$^{4a}$R$^{4a'}$, (CH$_2$)$_q$C(O)OR$^{4a}$, and a (CH$_2$)$_r$—C$_{3-10}$ carbocyclic residue substituted with 0–3 R$^{4c}$;

R$^{4a}$ and R$^{4a'}$, at each occurrence, are selected from H, C$_{1-6}$ alkyl, (CH$_2$)$_r$C$_{3-6}$ cycloalkyl, and phenyl;

R$^{4b}$, at each occurrence, is selected from C$_{1-6}$ alkyl, C$_{2-8}$ alkenyl, (CH$_2$)$_r$C$_{3-6}$ cycloalkyl, C$_{2-8}$ alkynyl, and phenyl;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$NR$^{4a}$R$^{4a'}$, and (CH$_2$)$_r$phenyl;

R$^{4d}$, is selected from H, C$_{1-6}$ alkyl, (CHR')$_q$OH, (CHR')$_q$OR$^{7a}$, (CHR')$_q$OC(O)R$^{7b}$, (CHR')$_q$OC(O)NHR$^{7a}$;

R$^5$ is selected from a (CR$^{5'}$R$^{5''}$)$_r$—C$_{3-10_{310}}$ carbocyclic residue substituted with 0–5 R$^{16_{16}}$ and a (CR$^{5'}$CR$^{5''}$)$_r$-5–10 membered heterocyclic system containing 1–4 heteroatoms selected from N, O, and S, substituted with 0–3 R$^{16_{16}}$;

R$^{5'5}$ and R$^{5''5}$, at each occurrence, are selected from H, C$_{1-6_{16}}$ alkyl, (CH$_2$)$_r$C$_{3-6_{36}}$ cycloalkyl, and phenyl;

R$^7$, is selected from H, C$_{1-6}$ alkyl, C$_{2-8}$ alkenyl, C$_{2-8}$ alkynyl, (CHR')$_q$OH, (CHR')$_q$SH, (CHR')$_q$OR$^{7d}$, (CHR')$_q$SR$^{7d}$, (CHR')$_q$NR$^{7a}$R$^{7a'}$, (CHR')$_q$C(O)OH, (CHR')$_r$C(O)R$^{7b}$, (CHR')$_q$C(O)NR$^{7a}$R$^{7a'}$, (CHR')$_q$NR$^{7a}$C(O)R$^{7a}$, (CHR')$_q$NR$^{7a}$C(O)H, (CHR')$_q$C(O)OR$^{7a}$, (CHR')$_q$OC(O)R$^{7b}$, (CHR')$_q$S(O)$_p$R$^{7b}$, (CHR')$_q$S(O)$_2$NR$^{7a}$R$^{7a'}$, (CHR')$_q$NR$^{7a}$S(O)$_2$R$^{7b}$, (CHR')$_q$NHC(O)NR$^{7a}$R$^{7a}$, (CHR')$_q$NHC(O)OR$^{7a}$, (CHR')$_q$OC(O)NHR$^{7a}$, C$_{1-6}$ haloalkyl, a (CHR')$_r$—C$_{3-10}$ carbocyclic residue substituted with 0–3 R$^{7c}$, and a (CHR')$_r$-5–10 membered heterocyclic system containing 1–4 heteroatoms selected from N, O, and S, substituted with 0–2 R$^{7c}$;

R$^{7a}$ and R$^{7a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{7e}$, and a (CH$_2$)$_r$-5–10 membered heterocyclic system containing 1–4 heteroatoms selected from N, O, and S, substituted with 0–3 R$^{7e}$;

R$^{7b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{7e}$, and a (CH$_2$)$_r$-5–6 membered heterocyclic system containing 1–4 heteroatoms selected from N, O, and S, substituted with 0–3 R$^{7e}$;

R$^{7c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{7f}$R$^{7f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{7b}$, (CH$_2$)$_r$C(O)NR$^{7f}$R$^{7f}$, (CH$_2$)$_r$NR$^{7f}$C(O)R$^{7a}$, (CH$_2$)$_r$C(O)OC$_{1-4}$ alkyl, (CH$_2$)$_r$OC(O)R$^{7b}$, (CH$_2$)$_r$C(=NR$^{7f}$)NR$^{7f}$R$^{7f}$, (CH$_2$)$_r$S(O)$_p$R$^{7b}$, (CH$_2$)$_r$NHC(=NR$^{7f}$)NR$^{7f}$R$^{7f}$, (CH$_2$)$_r$S(O)$_2$NR$^{7f}$R$^{7f}$, (CH$_2$)$_r$NR$^{7f}$S(O)$_2$R$^{7b}$, and (CH$_2$)$_r$phenyl substituted with 0–3 R$^{7e}$;

R$^{7d}$, at each occurrence, is selected from methyl, CF$_3$, C$_{2-6}$ alkyl substituted with 0–3 R$^{7e}$, and a C$_{3-10}$ carbocyclic residue substituted with 0–3 R$^{7c}$;

R$^{7e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, (CF$_2$)$_r$CF$_3$, (CH$_2$)$_r$OC$_{1-5}$ alkyl, (CH$_2$)$_q$OH, OH, (CH$_2$)$_q$SH, SH, (CH$_2$)$_r$SC$_{1-5}$ alkyl, (CH$_2$)$_q$NR$^{7f}$R$^{7f}$, and (CH$_2$)$_r$phenyl;

R$^{7f}$, at each occurrence, is selected from H, C$_{1-6}$ alkyl, and C$_{3-6}$ cycloalkyl;

R$^8$ is selected from H, C$_{1-6}$ alkyl, C$_{3-6}$ cycloalkyl, and (CH$_2$)$_r$phenyl substituted with 0–3 R$^{8a}$;

R$^{8a}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{7f}$R$^{7f}$, and (CH$_2$)$_r$phenyl;

alternatively, R$^7$ and R$^8$ join to form C$_{3-7}$ cycloalkyl, or =NR$^{8b}$;

R$^{8b}$ is selected from H, C$_{1-6}$ alkyl, C$_{3-6}$ cycloalkyl, OH, CN, and (CH$_2$)$_r$-phenyl;

R$^{11}$, is selected from H, C$_{1-6}$ alkyl, C$_{2-8}$ alkenyl, C$_{2-8}$ alkynyl, (CH$_2$)$_q$OH, (CH$_2$)$_q$SH, (CH$_2$)$_q$OR$^{11d}$, (CH$_2$)$_q$SR$^{11d}$, (CH$_2$)$_q$NR$^{11a}$R$^{11a'}$, (CH$_2$)$_r$C(O)OH, (CH$_2$)$_r$C(O)R$^{11b}$, (CH$_2$)$_r$C(O)NR$^{11a}$R$^{11a'}$, (CH$_2$)$_r$NR$^{11a}$C(O)R$^{11b}$, (CH$_2$)$_q$NR$^{11a}$C(O)NR$^{11a}$R$^{11a}$, (CH$_2$)$_r$C(O)OR$^{11a}$, (CH$_2$)$_q$OC(O)R$^{11b}$, (CH$_2$)$_q$S(O)$_p$R$^{11b}$, (CH$_2$)$_q$S(O)$_2$NR$^{11a}$R$^{11a'}$, (CH$_2$)$_q$NR$^{11a}$S(O)$_2$R$^{11b}$, C$_{1-6}$ haloalkyl, a (CH$_2$)$_r$—C$_{3-10}$ carbocyclic residue substituted with 0–5 R$^{11c}$, and a (CH$_2$)$_r$-5–10 membered heterocyclic system containing 1–4 heteroatoms selected from N, O, and S, substituted with 0–3 R$^{11c}$;

R$^{11a}$ and R$^{11a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{11e}$, and a (CH$_2$)$_r$-5–10 membered heterocyclic system containing 1–4 heteroatoms selected from N, O, and S, substituted with 0–3 R$^{11e}$;

R$^{11b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{11e}$, and a (CH$_2$)$_r$-5–6 membered heterocyclic system containing 1–4 heteroatoms selected from N, O, and S, substituted with 0–3 R$^{11e}$;

R$^{11c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{11f}$R$^{11f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{11b}$, (CH$_2$)$_r$C(O)NR$^{11f}$R$^{11f}$, (CH$_2$)$_r$NR$^{11f}$C(O)R$^{11a}$, (CH$_2$)$_r$C(O)OC$_{1-4}$ alkyl, (CH$_2$)$_r$OC(O)R$^{11b}$, (CH$_2$)$_r$C(=NR$^{11f}$)NR$^{11f}$R$^{11f}$, (CH$_2$)$_r$NHC(=NR$^{11f}$)NR$^{11f}$R$^{11f}$, (CH$_2$)$_r$S(O)$_p$R$^{11b}$, (CH$_2$)$_r$S(O)$_2$NR$^{11f}$R$^{11f}$, (CH$_2$)$_r$NR$^{11f}$S(O)$_2$R$^{11b}$, and (CH$_2$)$_r$phenyl substituted with 0–3 R$^{11e}$;

R$^{11d}$, at each occurrence, is selected from methyl, CF$_3$, C$_{2-6}$ alkyl substituted with 0–3 R$^{11e}$, C$_{3-6}$ alkenyl, C$_{3-6}$ alkynyl, and a C$_{3-10}$ carbocyclic residue substituted with 0–3 R$^{11c}$;

R$^{11e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{11f}$R$^{11f}$, and (CH$_2$)$_r$phenyl;

R$^{11f}$, at each occurrence, is selected from H, C$_{1-6}$ alkyl, and C$_{3-6}$ cycloalkyl;

R$^{15}$, at each occurrence, is selected from C$_{1-8}$ alkyl, (CH$_2$)$_r$C$_{3-6}$ cycloalkyl, Cl, Br, I, F, NO$_2$, CN, (CHR')$_r$NR$^{15a}$R$^{15a'}$, (CHR')$_r$OH, (CHR')$_r$O(CHR')$_r$R$^{15d}$, (CHR')$_r$SH, (CHR')$_r$C(O)H, (CHR')$_r$S(CHR')$_r$R$^{15d}$, (CHR')$_r$C(O)OH, (CHR')$_r$C(O)(CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$C(=NR$^{15f}$)NR$^{15a}$R$^{15a'}$, (CHR')$_r$NHC(=NR$^{15f}$)NR$^{15a}$R$^{15a'}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is selected from H, C$_{1-6}$ alkyl, C$_{2-8}$ alkenyl, C$_{2-8}$ alkynyl, (CH$_2$)$_r$C$_{3-6}$ cycloalkyl, and (CH$_2$)$_r$phenyl substituted with R$^{15e}$;

R$^{15a}$ and R$^{15a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{15e}$, and a (CH$_2$)$_r$-5–10 membered heterocyclic system containing 1–4 heteroatoms selected from N, O, and S, substituted with 0–2 R$^{15e}$;

R$^{15b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–3 R$^{15e}$, and (CH$_2$)$_r$-5–6 membered heterocyclic system containing 1–4 heteroatoms selected from N, O, and S, substituted with 0–2 R$^{15e}$;

R$^{15d}$, at each occurrence, is selected from C$_{3-8}$ alkenyl, C$_{3-8}$ alkynyl, methyl, CF$_3$, C$_{2-6}$ alkyl substituted with 0–3 R$^{15e}$, a (CH$_2$)$_r$—C$_{3-10}$ carbocyclic residue substituted with 0–3 R$^{15e}$, and a (CH$_2$)$_r$5–6 membered heterocyclic system containing 1–4 heteroatoms selected from N, O, and S, substituted with 0–3 R$^{15e}$;

R$^{15e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f}$, and (CH$_2$)$_r$phenyl;

R$^{15f}$, at each occurrence, is selected from H, C$_{1-6}$ alkyl, C$_{3-6}$ cycloalkyl, and phenyl;

R$^{16}$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$SH, (CHR')$_r$C(O)H, (CHR')$_r$S(CHR')$_r$R$^{16d}$, (CHR')$_r$C(O)OH, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$C(O)O(CHR')$_r$R$^{16d}$, (CHR')$_r$OC(O)(CHR')$_r$R$^{16b}$, (CHR')$_r$C(=NR$^{16f}$)NR$^{16a}$R$^{16a'}$, (CHR')$_r$NHC(=NR$^{16f}$)NR$^{16a}$R$^{16a'}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, C$_{2-8}$ alkenyl substituted with 0–3 R', C$_{2-8}$ alkynyl substituted with 0–3 R', and (CHR')$_r$phenyl substituted with 0–3 R$^{16e}$;

R$^{16a}$ and R$^{16a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

R$^{16b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–2 R$^{16e}$;

R$^{16d}$, at each occurrence, is selected from C$_{3-8}$ alkenyl, C$_{3-8}$ alkynyl, methyl, CF$_3$, C$_{2-6}$ alkyl substituted with 0–3

$R^{16e}$, a $(CH_2)_r$—$C_{3-10}$ carbocyclic residue substituted with 0–3 $R^{16e}$, and a $(CH_2)_r$-5–6 membered heterocyclic system containing 1–4 heteroatoms selected from N, O, and S, substituted with 0–3 $R^{16e}$;

$R^{16e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{16f}R^{16f}$, and $(CH_2)_r$phenyl;

$R^{16f}$, at each occurrence, is selected from H, $C_{1-5}$ alkyl, and $C_{3-6}$ cycloalkyl, and phenyl;

$R^{17}$, is selected from H, $C_{1-6}$ alkyl, $C_{2-8}$ alkenyl, $C_{2-8}$ alkynyl, $(CH_2)_qOH$, $(CH_2)_qSH$, $(CH_2)_qOR^{17d}$, $(CH_2)_q$ $SR^{17d}$, $(CH_2)_qNR^{17a}R^{17a'}$, $(CH_2)_rC(O)OH$, $(CH_2)_rC(O)$ $R^{17b}$, $(CH_2)_rC(O)NR^{17a}R^{17a'}$, $(CH_2)_rNR^{17a}C(O)R^{17b}$, $(CH_2)_qNR^{17a}C(O)H$, $(CH_2)_rC(O)OR^{17a}$, $(CH_2)_qOC(O)$ $R^{17b}$, $(CH_2)_qS(O)_pR^{17b}$, $(CH_2)_qS(O)_2NR^{17a}R^{17a'}$, $(CH_2)_q$ $NR^{17a}S(O)_2R^{17b}$, $C_{1-6}$ haloalkyl, a $(CH_2)_r$—$C_{3-10}$ carbocyclic residue substituted with 0–3 $R^{17c}$, and a $(CH_2)_r$-5–10 membered heterocyclic system containing 1–4 heteroatoms selected from N, O, and S, substituted with 0–2 $R^{17c}$;

$R^{17a}$ and $R^{17a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{17e}$, and a $(CH_2)_r$-5–10 membered heterocyclic system containing 1–4 heteroatoms selected from N, O, and S, substituted with 0–3 $R^{17e}$;

$R^{17b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{17e}$, and a $(CH_2)_r$-5–6 membered heterocyclic system containing 1–4 heteroatoms selected from N, O, and S, substituted with 0–3 $R^{17e}$;

$R^{17c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{17f}R^{17f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{17b}$, $(CH_2)_rC(O)NR^{17f}R^{17f}$, $(CH_2)_rNR^{17f}C$ $(O)R^{17a}$, $(CH_2)_rC(O)OC_{1-4}$ alkyl, $(CH_2)_rOC(O)R^{17b}$, $(CH_2)_rC(=NR^{17f})NR^{17f}R^{17f}$, $(CH_2)_rS(O)_pR^{17b}$, $(CH_2)_r$ $NHC(=NR^{17f})NR^{17f}R^{17f}$, $(CH_2)_rS(O)_2NR^{17f}R^{17f}$, $(CH_2)_r$ $NR^{17f}S(O)_2R^{17b}$, and $(CH_2)_r$phenyl substituted with 0–3 $R^{17e}$;

$R^{17d}$, at each occurrence, is selected from methyl, $CF_3$, $C_{2-6}$ alkyl substituted with 0–3 $R^{17e}$, $C_{3-6}$ alkenyl, $C_{3-6}$ alkynyl, and a $C_{3-10}$ carbocyclic residue substituted with 0–3 $R^{17c}$;

$R^{17e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{17f}R^{17f}$, and $(CH_2)_r$phenyl;

$R^{17f}$, at each occurrence, is selected from H, $C_{1-6}$ alkyl, and $C_{3-6}$ cycloalkyl;

$R^{18}$, is selected from H, $C_{1-6}$ alkyl, $C_{2-8}$ alkenyl, $C_{2-8}$ alkynyl, $(CHR')_qOH$, $(CHR')_qSH$, $(CHR')_qOR^{18d}$, $(CHR')_qSR^{18d}$, $(CHR')_qNR^{18a}R^{18a'}$, $(CHR')_rC(O)OH$, $(CHR')_rC(O)R^{18b}$, $(CHR')_rC(O)NR^{18a}R^{18a'}$, $(CHR')_q$ $NR^{18a}C(O)R^{18a}$, $(CHR')_qNR^{18a}C(O)H$, $(CHR')_rC(O)$ $OR^{18a}$, $(CHR')_qOC(O)R^{18b}$, $(CHR')_qS(O)_pR^{18b}$, $(CHR')_q$ $S(O)_2NR^{18a}R^{18a'}$, $(CHR')_qNR^{18a}S(O)_2R^{18b}$, $C_{1-6}$ haloalkyl, a $(CHR')_r$—$C_{3-10}$ carbocyclic residue substituted with 0–3 $R^{18c}$, and a $(CHR')_r$-5–10 membered heterocyclic system containing 1–4 heteroatoms selected from N, O, and S, substituted with 0–2 $R^{18c}$;

$R^{18a}$ and $R^{18a'}$, at each occurrence, are selected from H, $C_{1-6}$ alkyl, $C_{3-8}$ alkenyl, $C_{3-8}$ alkynyl, a $(CH_2)_r$—$C_{3-10}$ carbocyclic residue substituted with 0–5 $R^{18e}$, and a $(CH_2)_r$-5–10 membered heterocyclic system containing 1–4 heteroatoms selected from N, O, and S, substituted with 0–3 $R^{18e}$;

$R^{18b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0–2 $R^{18e}$, and a $(CH_2)_r$-5–6 membered heterocyclic system containing 1–4 heteroatoms selected from N, O, and S, substituted with 0–3 $R^{18e}$;

$R^{18c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{18f}R^{18f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{18b}$, $(CH_2)_rC(O)NR^{18f}R^{18f}$, $(CH_2)_rNR^{18f}C$ $(O)R^{18a}$, $(CH_2)_rC(O)OC_{1-4}$ alkyl, $(CH_2)_rOC(O)R^{18b}$, $(CH_2)_rC(=NR^{18f})NR^{18f}R^{18f}$, $(CH_2)_rS(O)_pR^{18b}$, $(CH_2)_r$ $NHC(=NR^{18f})NR^{18f}R^{18f}$, $(CH_2)_rS(O)_2NR^{18f}R^{18f}$, $(CH_2)_r$ $NR^{18f}S(O)_2R^{18b}$, and $(CH_2)_r$phenyl substituted with 0–3 $R^{18e}$;

$R^{18d}$, at each occurrence, is selected from methyl, $CF_3$, $C_{2-6}$ alkyl substituted with 0–3 $R^{18e}$, $C_{3-6}$ alkenyl, $C_{3-6}$ alkynyl, and a $C_{3-10}$ carbocyclic residue substituted with 0–3 $R^{18c}$;

$R^{18e}$, at each occurrence, is selected from $C_{1-6}$ alkyl, $C_{2-8}$ alkenyl, $C_{2-8}$ alkynyl, $C_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_r$ $SC_{1-5}$ alkyl, $(CH_2)_rNR^{18f}R^{18f}$, and $(CH_2)_r$phenyl;

$R^{18f}$, at each occurrence, is selected from H, $C_{1-6}$ alkyl, and $C_{3-6}$ cycloalkyl;

$R^{19}$ is selected from $C_{1-8}$ alkyl, $C_{3-8}$ alkenyl, $C_{3-8}$ alkynyl, —$C(O)R^{19b}$, —$C(O)NR^{19a}R^{19a}$, —$C(O)OR^{19a}$, and —$SO_2R^{19a}$, a $(CHR')_r$—$C_{3-10}$ carbocyclic residue substituted with 0–3 $R^{16}$, and a $(CHR')_r$-5–10 membered heterocyclic system containing 1–4 heteroatoms selected from N, O, and S, substituted with 0–2 $R^{16}$;

$R^{19a}$ is selected from $C_{1-8}$ alkyl, $C_{3-8}$ alkenyl, $C_{3-8}$ alkynyl, $C_{3-6}$ cycloalkyl, a $(CR^{5'}R^{5''})_r$—$C_{3-10{310}}$ carbocyclic residue substituted with 0–5 $R^{1516}$ and a $(CR^{5'}CR^{5''5})_r$-5–10 membered heterocyclic system containing 1–4 heteroatoms selected from N, O, and S, substituted with 0–3 $R^{1616}$;

$R^{19b}$ is selected from H, $C_{1-8}$ alkyl, $C_{3-8}$ alkenyl, $C_{3-8}$ alkynyl, $C_{3-6}$ cycloalkyl, a $(CR^{5'}R^{5''})_r$—$C_{3-10{310}}$ carbocyclic residue substituted with 0–5 $R^{1516}$ and a $(CR^{5'}CR^{5''})_r$-5–10 membered heterocyclic system containing 1–4 heteroatoms selected from N, O, and S, substituted with 0–3 $R^{1616}$;

m, at each occurrence, is selected from 1, 2, 3, 4, and 5;
n, at each occurrence, is selected from 0, 1, 2, 3, 4, and 5;
o, at each occurrence, is selected from 1 and 2;
p, at each occurrence, is selected from 1 and 2;
r, at each occurrence, is selected from 0, 1, 2, 3, 4, and 5;
q, at each occurrence, is selected from 1, 2, 3, 4, and 5;
s, at each occurrence, is selected from 0, 1, and 2;
t, at each occurrence, is selected from 0, 1, 2, 3, 4, and 5;
u, at each occurrence, is independently selected from 0, 1, and 2;
v, at each occurrence, is selected from 0 and 1; and
w, at each occurrence, is selected from 0, 1, 2, and 3.

[2] In another embodiment, the present invention provides novel compounds of formula (I), wherein:

$R^{4'}$ is absent or, taken with the nitrogen to which it is attached to form an N-oxide;

$R^7$, is selected from H, $C_{1-6}$ alkyl, $C_{2-8}$ alkenyl, $C_{2-8}$ alkynyl, $(CHR')_qOH$, $(CHR')_qOR^{7d}$, $(CHR')_qNR^{7a}R^{7a'}$, $(CHR')_qC$ $(O)R^{7b}$, $(CHR')_qC(O)NR^{7a}R^{7a'}$, $(CHR')_qNR^{7a}C(O)R^{7b}$, $(CHR')_qNR^{7a}C(O)H$, $(CHR')_qS(O)_2NR^{7a}R^{7a'}$, $(CHR')_q$ $NR^{7a}S(O)_2R^{7b}$, $(CHR')_qNHC(O)NHR^{7a}$, $(CHR')_qNHC (O)OR$^{7a}$, (CHR')$_q$OC(O)NHR$^{7a}$, C$_{1-6}$ haloalkyl, a (CHR')$_r$—C$_{3-10}$ carbocyclic residue substituted with 0–3 R$^{7c}$, and a (CHR')$_r$-5–10 membered heterocyclic system containing 1–4 heteroatoms selected from N, O, and S, substituted with 0–2 R$^{7c}$;

alternatively, R$^7$ and R$^8$ join to form C$_{3-7}$ cycloalkyl, or =NR$^{8b}$;

R$^{11}$, is selected from H, C$_{1-6}$ alkyl, C$_{2-8}$ alkenyl, C$_{2-8}$ alkynyl, (CH$_2$)$_q$OH, (CH$_2$)$_q$OR$^{11d}$, (CH$_2$)$_q$NR$^{11a}$R$^{11a'}$, (CH$_2$)$_r$C(O)R$^{11b}$, (CH$_2$)$_r$C(O)NR$^{11a}$R$^{11a'}$, (CH$_2$)$_q$NR$^{11a}$C(O)R$^{11b}$, (CH$_2$)$_q$NR$^{11a}$C(O)NHR$^{11a}$, (CH$_2$)$_q$NHC(O)NHR$^{11a}$, (CH$_2$)$_q$NHC(O)OR$^{11a}$, (CH$_2$)$_q$OC(O)NHR$^{11a}$, C$_{1-6}$ haloalkyl, a (CH$_2$)$_r$—C$_{3-10}$ carbocyclic residue substituted with 0–5 R$^{11c}$, and a (CH$_2$)$_r$-5–10 membered heterocyclic system containing 1–4 heteroatoms selected from N, O, and S, substituted with 0–3 R$^{11c}$.

[3] In another embodiment, the present invention provides novel compounds of formula (I), wherein:

A is selected from

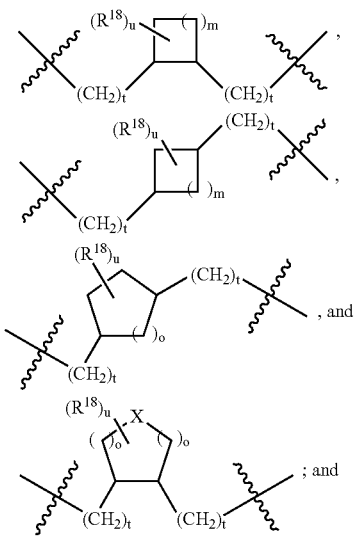

t is selected from 0, 1, and 2.

[4] In another embodiment, the present invention provides novel compounds of formula (I), wherein:

R$^{17}$ is selected from H; and

R$^{18}$ is selected from H.

[5] In another embodiment, the present invention provides novel compounds of formula (I), wherein:

A is selected from

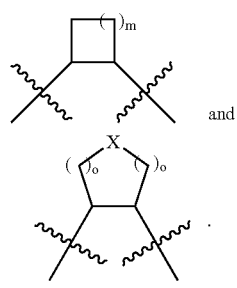

[6] In another, the present invention provides novel compounds of formula (I) wherein:

G is selected from —C(O)R$^3$, —C(O)NR$^2$R$^3$, —C(O)OR$^3$, —SO$_2$NR$^2$R$^3$, and —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, C(=C(CN)$_2$)NR$^2$R$^3$, and

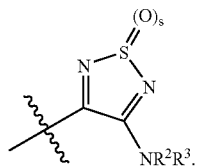

[7]. In another embodiment, the present invention provides novel compounds of formula (I), wherein:

G is selected from —C(O)NR$^2$R$^3$, $^{23}$C(=NR$^{1a}$)NR$^2$R$^3$, C(=CHCN)NR$^2$R$^3$, C(=CHNO$_2$)NR$^2$R$^3$, and C(=C(CN)$_2$)NR$^2$R$^3$;

[8] In another embodiment, the present invention provides novel compounds of formula (I), wherein:

R$^{16}$, at each occurrence, is selected from methyl, ethyl, propyl, iso-propyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0–3 R$^{16e}$;

R$^{16a}$ and R$^{16a'}$, at each occurrence, are selected from H, methyl, ethyl, and a (CH$_2$)$_r$—C$_{3-6}$ carbocyclic residue substituted with 0–2 R$^{16e}$;

R$^{16e}$, at each occurrence, is selected from methyl, ethyl, Cl, F, Br, I, CN, CF$_3$, and OCH$_3$;

R$^{16f}$, at each occurrence, is selected from H; and r is selected from 0, 1, and 2.

[9] In another embodiment, the present invention provides novel compounds of formula (I), wherein:

R$^3$ is selected from a (CR$^{3'}$R$^{3''}$)$_r$—C$_{3-6}$ carbocyclic residue substituted with 0–2 R$^{15}$ and a (CR$^{3'}$CR$^{3''}$)$_r$-5–10 membered heterocyclic system containing 1–4 heteroatoms selected from N, O, and S, subsituted with 0–2 R$^{15}$;

R$^{3'}$ and R$^{3''}$, at each occurrence, are selected from H;

R$^{15}$, at each occurrence, is selected from C$_{1-8}$ alkyl, (CH$_2$)$_r$C$_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O)(CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15f}$R$^{15f}$, (CHR')$_r$C(O)O(CHR')$_r$R$^{15d}$, (CHR')$_r$OC(O)(CHR')$_r$R$^{15b}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is selected from H, and C$_{1-6}$ alkyl;

R$^{15a}$ and R$^{15a'}$, at each occurrence, are selected from H, C$_{1-6}$ alkyl, a (CH$_2$)$_r$—C$_{3-6}$ carbocyclic residue substituted with 0–5 R$^{15e}$, and a (CH$_2$)$_r$-5–6 membered heterocyclic system containing 1–2 heteroatoms selected from N, O, and S, substituted with 0–2 R$^{15e}$;

R$^{15b}$, at each occurrence, is selected from C$_{1-6}$ alkyl, a (CH$_2$)$_r$—C$_{3-6}$ carbocyclic residue substituted with 0–3 R$^{15e}$, and (CH$_2$)$_r$-5–6 membered heterocyclic system containing 1–2 heteroatoms selected from N, O, and S, substituted with 0–2 $R^{15e}$; and $R^{15e}$, at each occurrence, is selected from $C_{1-6}$ alkyl, Cl, F, Br, I, CN, $(CF_2)_rCF_3$, and OH.

[10] In another embodiment, the present invention provides novel compounds of formula (I), wherein:
G is selected from

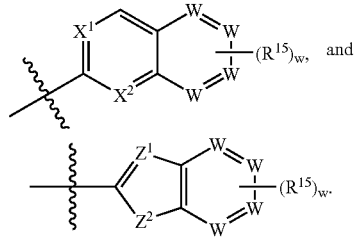

[11] In another embodiment, the present invention provides novel compounds of formula (I), wherein:
$R^1$ is selected from H;
both $X^1$ and $X^2$ cannot be C; and
$Z^2$ is selected from $NR^{1'}$, O, and S.

[12] In a further embodiment, the present invention provides novel compounds of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0–3 $R^{16e}$;
$R^{16a}$ and $R^{16a'}$, at each occurrence, are selected from H, methyl, ethyl, and a $(CH_2)_r$—$C_{3-6}$ carbocyclic residue substituted with 0–2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

[13] In another embodiment, the present invention provides novel compounds of formula (I), wherein:
$R^{15}$, at each occurrence, is selected from $C_{1-8}$ alkyl, $(CH_2)_r$ $C_{3-6}$ cycloalkyl, Cl, Br, F, CN, $(CHR')_rNR^{15a}R^{15a'}$, $(CHR')_rOH$, $(CHR')_rO(CHR')_rR^{15d}$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rNR^{15f}C(O)NR^{15a}R^{15f}$, $(CHR')_rC(O)O(CHR')_rR^{15d}$, $(CHR')_rOC(O)(CHR')_rR^{15b}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$ haloalkyl, $C_{2-8}$ alkenyl, $C_{2-8}$ alkynyl, $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;
R', at each occurrence, is selected from H, and $C_{1-6}$ alkyl;
$R^{15a}$ and $R^{15a'}$, at each occurrence, are selected from H, $C_{1-6}$ alkyl, a $(CH_2)_r$—$C_{3-6}$ carbocyclic residue substituted with 0–5 $R^{15e}$, and a $(CH_2)_r$-5–6 membered heterocyclic system containing 1–2 heteroatoms selected from N, O, and S, substituted with 0–2 $R^{15e}$;
$R^{15b}$, at each occurrence, is selected from $C_{1-6}$ alkyl, a $(CH_2)_r$—$C_{3-6}$ carbocyclic residue substituted with 0–3 $R^{15e}$, and $(CH_2)_r$-5–6 membered heterocyclic system containing 1–2 heteroatoms selected from N, O, and S, substituted with 0–2 $R^{15e}$; and $R^{15e}$, at each occurrence, is selected from $C_{1-6}$ alkyl, Cl, F, Br, I, CN, $(CF_2)_rCF_3$, and OH.

[14] In another embodiment, the present invention provides novel compounds of formula (I), wherein:
A is selected from

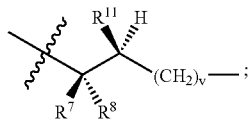

v is selected from 0 and 1.

[15] In another embodiment, the present invention provides novel compounds of formula (I) wherein:
G is selected from —$C(O)R^3$, —$C(O)NR^2R^3$, —$C(O)OR^3$, —$SO_2NR^2R^3$, and —$SO_2R^3$, —$C(=S)NR^2R^3$, $C(=NR^{1a})NR^2R^3$, $C(=CHCN)NR^2R^3$, $C(=CHNO_2)NR^2R^3$, $C(=C(CN)_2)NR^2R^3$, and

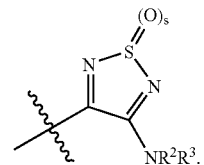

[16]. In another embodiment, the present invention provides novel compounds of formula (I), wherein:
G is selected from —$C(O)NR^2R^3$, $^{23}C(=NR^{1a})NR^2R^3$, $C(=CHCN)NR^2R^3$, $C(=CHNO_2)NR^2R^3$, and $C(=C(CN)_2)NR^2R^3$.

[17] In another embodiment, the present invention provides novel compounds of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0–3 $R^{16e}$;
$R^{16a}$ and $R^{16a'}$, at each occurrence, are selected from H, methyl, ethyl, and a $(CH_2)_r$—$C_{3-6}$ carbocyclic residue substituted with 0–2 $R^{16e}$;
$R^{16e}$, at each occurrence, is selected from methyl, ethyl, Cl, F, Br, I, CN, $CF_3$, and $OCH_3$;
$R^{16f}$, at each occurrence, is selected from H; and
r is selected from 0, 1, and 2.

[18] In another embodiment, the present invention provides novel compounds of formula (I), wherein:
$R^3$ is selected from a $(CR^{3'}R^{3''})_r$—$C_{3-6}$ carbocyclic residue substituted with 0–2 $R^{15}$ and a $(CR^{3'}CR^{3''})_r$-5–10 membered heterocyclic system containing 1–4 heteroatoms selected from N, O, and S, subsituted with 0–2 $R^{15}$
$R^{3'}$ and $R^{3''}$, at each occurrence, are selected from H;
$R^{15}$, at each occurrence, is selected from $C_{1-8}$ alkyl, $(CH_2)_r$ $C_{3-6}$ cycloalkyl, Cl, Br, F, CN, $(CHR')_rNR^{15a}R^{15a'}$, $(CHR')_rOH$, $(CHR')_rO(CHR')_rR^{15d}$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rNR^{15f}C(O)NR^{15a}R^{15a'}$, $(CHR')_rC(O)O(CHR')_rR^{15d}$, $(CHR')_rOC(O)(CHR')_rR^{15b}$, $(CHR')_rS(O)_p(CHR')_rR^{15b}$, $(CHR')_rS(O)_2NR^{15a}R^{15a'}$, $(CHR')_r$ $NR^{15f}S(O)_2$ $(CHR')_rR^{15b}$, $C_{1-6}$ haloalkyl, $C_{2-8}$ alkenyl substituted with 0–3 R', $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0–5 $R^{15e}$, and a $(CH_2)_r$-5–6 membered heterocyclic system containing 1–2 heteroatoms selected from N, O, and S, substituted with 0–2 $R^{15e}$;

$R^{15b}$, at each occurrence, is selected from $C_{1-6}$ alkyl, a $(CH_2)_r$—$C_{3-6}$ carbocyclic residue substituted with 0–3 $R^{15e}$, and $(CH_2)_r$-5–6 membered heterocyclic system containing 1–2 heteroatoms selected from N, O, and S, substituted with 0–2 $R^{15e}$; and $R^{15e}$, at each occurrence, is selected from $C_{1-6}$ alkyl, Cl, F, Br, I, CN, $(CF_2)_rCF_3$, and OH.

[19] In a further embodiment, the present invention provides novel compounds of formula (I), wherein:
G is selected from

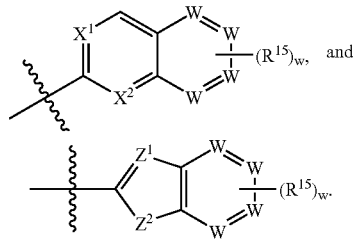

[20] In a further embodiment, the present invention provides novel compounds of formula (I), wherein:
$R^1$ is H;
both $X^1$ and $X^2$ cannot be C; and
$Z^2$ is selected from $NR^{1'}$, O, and S.

[21] In a further embodiment, the present invention provides novel compounds of formula (I), wherein:
$R^{16}$, at each occurrence, is selected from methyl, ethyl, propyl, iso-propyl, $C_{2-8}$ alkenyl, $C_{2-8}$ alkynyl, $(CH_2)_rC_{3-6}$ cycloalkyl, Cl, Br, I, F, $NO_2$, CN, $(CHR')_rNR^{16a}R^{16a'}$, $(CHR')_rOH$, $(CHR')_rO(CHR')_rR^{16d}$, $(CHR')_rC(O)(CHR')_rR^{16b}$, $(CHR')_rC(O)NR^{16a}R^{16a'}$, $(CHR')_rNR^{16f}C(O)(CHR')_rR^{16b}$, $(CHR')_rS(O)_p(CHR')_rR^{16b}$, $(CHR')_rS(O)_2NR^{16a}R^{16a'}$, $(CHR')_rNR^{16f}S(O)_2(CHR')_rR^{16b}$, $C_{1-6}$ haloalkyl, and $(CHR')_r$phenyl substituted with 0–3 $R^{16e}$;

$R^{16a}$ and $R^{16a'}$, at each occurrence, are selected from H, methyl, ethyl, and a $(CH_2)_r$—$C_{3-6}$ carbocyclic residue substituted with 0–2 $R^{16e}$;

$R^{16e}$, at each occurrence, is selected from methyl, ethyl, Cl, F, Br, I, CN, $CF_3$, and $OCH_3$;

$R^{16f}$, at each occurrence, is selected from H; and
r is selected from 0, 1, and 2.

[22] In another embodiment, the present invention provides novel compounds of formula (I), wherein:
$R^{15}$, at each occurrence, is selected from $C_{1-8}$ alkyl, $(CH_2)_r$ $C_{3-6}$ cycloalkyl, Cl, Br, F, CN, $(CHR')_rNR^{15a}R^{15a'}$, $(CHR')_rOH$, $(CHR')_rO(CHR')_rR^{15d}$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rNR^{15f}C(O)NR^{15a}R^{15a'}$, $(CHR')_rC(O)O(CHR')_rR^{15d}$, $(CHR')_rOC(O)(CHR')_rR^{15b}$, $(CHR')_rS(O)_p(CHR')_rR^{15b}$, $(CHR')_rS(O)_2NR^{15a}R^{15a'}$, $(CHR')_rNR^{15f}S(O)_2$ $(CHR')_rR^{15b}$, $C_{1-6}$ haloalkyl, $C_{2-8}$ alkenyl substituted with 0–3 $R_1$, $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$;

R', at each occurrence, is selected from H, and $C_{1-6}$ alkyl;

$R^{15a}$ and $R^{15a'}$, at each occurrence, are selected from H, $C_{1-6}$ alkyl, a $(CH_2)_r$—$C_{3-6}$ carbocyclic residue substituted with 0–5 $R^{15e}$, and a $(CH_2)_r$-5–6 membered heterocyclic system containing 1–2 heteroatoms selected from N, O, and S, substituted with 0–2 $R^{15e}$;

$R^{15b}$, at each occurrence, is selected from $C_{1-6}$ alkyl, a $(CH_2)_r$—$C_{3-6}$ carbocyclic residue substituted with 0–3 $R^{15e}$, and $(CH_2)_r$-5–6 membered heterocyclic system containing 1–2 heteroatoms selected from N, O, and S, substituted with 0–2 $R^{15e}$; and $R^{15e}$, at each occurrence, is selected from $C_{1-6}$ alkyl, Cl, F, Br, I, CN, $(CF_2)_rCF_3$, and OH.

[23] In a further embodiment, the present invention provides novel compounds of formula (I), wherein the compound of formula I is selected from:

N-(3-acetylphenyl)-N'-[(2R)-2-[[cis-4-[(4-fluorophenyl)methyl]-1-cyclohexyl]amino]-(1R)-1-cyclohexyl]urea hydrochloride;

N-(3-acetylphenyl)-N'-[(2R)-2-[[trans-4-[(4-fluorophenyl)methyl]-1-cyclohexyl]amino]-(1R)-1-cyclohexyl]urea hydrochloride;

N-(3-cyanophenyl)-N'-[(2R)-2-[[trans-4-[(4-fluorophenyl)methyl]-1-cyclohexyl]amino]-(1R)-1-cyclohexyl]urea trifluoroacetate;

N-(3-cyanophenyl)-N'-[(2R)-2-[[cis-4-[(4-fluorophenyl)methyl]-1-cyclohexyl]amino]-(1R)-1-cyclohexyl]urea trifluoroacetate;

N-(3-cyanophenyl)-N'-[(2S)-2-[[trans-4-[(4-fluorophenyl)methyl]-1-cyclohexyl]amino]-(1S)-1-cyclohexyl]urea trifluoroacetate;

N-(3-cyanophenyl)-N'-[(2S)-2-[[cis-4-[(4-fluorophenyl)methyl]-1-cyclohexyl]amino]-(1S)-1-cyclohexyl]urea trifluoroacetate;

N-(3-acetylphenyl)-N'-[(2S)-2-[[trans-4-[(4-fluorophenyl)methyl]-1-cyclohexyl]amino]-(1S)-1-cyclohexyl]urea trifluoroacetate;

N-(3-acetylphenyl)-N'-[(2S)-2-[[cis-4-[(4-fluorophenyl)methyl]-1-cyclohexyl]amino]-(1S)-1-cyclohexyl]urea trifluoroacetate;

N-(3-acetylphenyl)-N'-[(2R)-2-[[(3R)-3-[(4-fluorophenyl)methyl]-(1R)-1-cyclohexyl]amino]-(1R)-1-cyclohexyl]urea;

N-(3-acetylphenyl)-N'-[(2R)-2-[[(3R)-3-[(4-fluorophenyl)methyl]-(1S)-1-cyclohexyl]amino]-(1R)-1-cyclohexyl]urea;

N-(3-acetylphenyl)-N'-[(2R)-2-[[(3S)-3-[(4-fluorophenyl)methyl]-(1R)-1-cyclohexyl]amino]-(1R)-1-cyclohexyl]urea;

N-(3-acetylphenyl)-N'-[(2R)-2-[[(3S)-3-[(4-fluorophenyl)methyl]-(1S)-1-cyclohexyl]amino]-(1R)-1-cyclohexyl]urea;

N-(4-fluorophenyl)-N'-[(2R)-2-[[(3R)-3-[(4-fluorophenyl)methyl]-(1R)-1-cyclohexyl]amino]-(1R)-1-cyclohexyl]urea;

N-(4-fluorophenyl)-N'-[(2R)-2-[[(3R)-3-[(4-fluorophenyl)methyl]-(1S)-1-cyclohexyl]amino]-(1R)-1-cyclohexyl]urea;

N-(4-fluorophenyl)-N'-[(2R)-2-[[(3S)-3-[(4-fluorophenyl)methyl]-(1R)-1-cyclohexyl]amino]-(1R)-1-cyclohexyl]urea;

N-(4-fluorophenyl)-N'-[(2R)-2-[[(3S)-3-[(4-fluorophenyl)methyl]-(1S)-1-cyclohexyl]amino]-(1R)-1-cyclohexyl]urea;

N-(3-acetylphenyl)-N'-((3S,4S)-4-{[4-(4-fluorobenzyl)cyclohexyl]amino}tetrahydro-3-furanyl)urea;

N-(3-acetylphenyl)-N'-({(2S)-1-[4-(4-fluorobenzyl)cyclohexyl]pyrrolidinyl}methyl)urea;

N-(3-acetylphenyl)-N'-({(2S)-1-[4-(4-fluorobenzyl)cyclohexyl]pyrrolidinyl}methyl)urea;

N-(3-acetylphenyl)-N'-({(2R)-1-[4-(4-fluorobenzyl)cyclohexyl]pyrrolidinyl}methyl)urea;

N-(3-acetylphenyl)-N'-({(2R)-1-[4-(4-fluorobenzyl)cyclohexyl]pyrrolidinyl}methyl)urea;

N-(3-acetylphenyl)-N'-{(3R)-1-[4-(4-fluorobenzyl)cyclohexyl]pyrrolidinyl}urea;

N-(3-acetylphenyl)-N'-{(3R)-1-[4-(4-fluorobenzyl)cyclohexyl]pyrrolidinyl}urea;

N-(3-acetylphenyl)-N'-{(3S)-1-[4-(4-fluorobenzyl)cyclohexyl]pyrrolidinyl}urea; and N-(3-acetylphenyl)-N'-{(3S)-1-[4-(4-fluorobenzyl)cyclohexyl]pyrrolidinyl}urea.

[24] In a third embodiment, the present invention provides a pharmaceutical composition, comprising a pharmaceutically acceptable carrier and a therapeutically effective amount of a compound of the present invention.

[25] In a fourth embodiment, the present invention provides a method for modulation of chemokine receptor activity comprising administering to a patient in need thereof a therapeutically effective amount of the compounds of the present invention.

[26] In another embodiment, the present invention provides a method for treating or preventing inflammatory diseases, comprising administering to a patient in need thereof a therapeutically effective amount of the compounds of the present invention.

[27] In another embodiment, the present invention provides a method for treating or preventing asthma, comprising administering to a patient in need thereof a therapeutically effective amount of a compound of the present invention.

In another embodiment, G is selected from —C(O)R³, —C(O)NR²R³, —C(O)OR³, —SO₂NR²R³, —SO₂R³, —C(=S)NR²R³, C(=NR¹ᵃ)NR²R³, C(=CHCN)NR²R³, C(=CHNO₂)NR²R³, C(=C(CN)₂)NR²R³, and

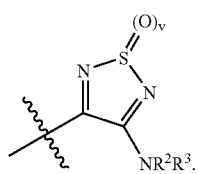

In another embodiment, G is selected from —C(O)NR²R³, C(=CHCN)NR²R³, C(=CHNO₂)NR²R³, and C(=C(CN)₂)NR²R³.

In another embodiment, G is selected from —C(O)NR²R³.

In another embodiment, G is selected from

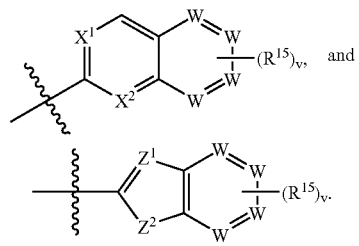

In another embodiment, $R^1$, $R^{1'}$, and $R^2$ are equal to H.

In another embodiment, $R^3$ is selected from a $(CR^{3'}R^{3''})_r$—$C_{3-6}$ carbocyclic residue substituted with 0–2 $R^{15}$ and a $(CR^{3'}CR^{3''})_r$-5–10 membered heterocyclic system containing 1–4 heteroatoms selected from N, O, and S, substituted with 0–3 $R^{15}$.

In another embodiment, $R^3$ is selected from a $(CR^{3'}R^{3''})_r$—$C_{3-6}$ carbocyclic residue substituted with 0–2 $R^{15}$.

In another embodiment, $R^3$ is phenyl substituted with 0–2 $R^{15}$.

In another embodiment, $R^4$ is absent.

In another embodiment, $R^{15}$, at each occurrence, is selected from $C_{1-8}$ alkyl, $(CH_2)_rC_{3-6}$ cycloalkyl, Cl, Br, F, CN, $(CHR')_rNR^{15a}R^{15a'}$, $(CHR')_rOH$, $(CHR')_rO(CHR')_rR^{15d}$, $(CHR')_rC(O)(CHR')_rR^{15b}$, $(CHR')_rC(O)NR^{15a}R^{15a'}$, $(CHR')_rNR^{15f}C(O)(CHR')_rR^{15b}$, $(CHR')_rNR^{15f}C(O)NR^{15a}R^{15a'}$, $(CHR')_rC(O)O(CHR')_rR^{15d}$, $(CHR')_rOC(O)(CHR')_rR^{15b}$, $(CHR')_rS(O)_p(CHR')_rR^{15b}$, $(CHR')_rS(O)_2NR^{15a}R^{15a'}$, $(CHR')_rNR^{15f}S(O)_2(CHR')_rR^{15b}$, $C_{1-6}$ haloalkyl, $C_{2-8}$ alkenyl substituted with 0–3 $R_1$, $C_{2-8}$ alkynyl substituted with 0–3 R', $(CHR')_r$phenyl substituted with 0–3 $R^{15e}$, and a $(CH_2)_r$-5–10 membered heterocyclic system containing 1–4 heteroatoms selected from N, O, and S, substituted with 0–2 $R^{15e}$.

The invention may be embodied in other specific forms without departing from the spirit or essential attributes thereof. This invention also encompasses all combinations of preferred aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^a$) occurs more than one time in any constituent or formula for a compound, its definition at each occurrence is independent of its definition at every other occurrence. Thus, for example, if a group is shown to be substituted with 0–2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. $C_{2-10}$ alkenyl, is intended to include $C_2$, $C_3$, $C_4$, $C_5$, $C_6$, $C_7$, $C_8$, $C_9$, and $C_{10}$ alkenyl groups. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Alkynyl" is intended to include hydrocarbon chains of either a straight or branched configuration and one or more unsaturated triple carbon-carbon bonds which may occur in any stable point along the chain, such as ethynyl, propynyl, and the like. $C_{2-10}$ alkynyl, is intended to include $C_2$, $C_3$, $C_4$, $C_5$, $C_6$, $C_7$, $C_8$, $C_9$, and $C_{10}$ alkynyl groups. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-7}$ cycloalkyl, is intended to include $C_3$, $C_4$, $C_5$, $C_6$, and $C_7$ cycloalkyl groups.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, the term "5–6-membered cyclic ketal" is intended to mean 2,2-disubstituted 1,3-dioxolane or 2,2-disubstituted 1,3-dioxane and their derivatives.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl(tetralin).

As used herein, the term "heterocycle" or "heterocyclic system" is intended to mean a stable 4, 5, 6, or 7-membered monocyclic or bicyclic or 7, 8, 9, or 10-membered bicyclic heterocyclic ring which is saturated, partially unsaturated, or unsaturated (aromatic), and which consists of carbon atoms and 1, 2, 3, or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl., oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. Preferred heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same.

"Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

The term "therapeutically effective amount" of a compound of this invention means an amount alone or in combination with other active ingredients or an amount the combination of compounds claimed effective to modulate chemokine receptor activity or treat the symptoms of asthma or an allergic disorder in a host.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents that are compatible with the reaction conditions will be readily apparent to one skilled in the art and alternate methods must be used. It will also be recognized that another major consideration in the planning of any synthetic route in this field is the judicious choice of the protecting group used for the protection of the reactive functional groups present in the compounds described in this invention. An authoritative account describing the many alternatives to the trained practitioner is Greene and Wuts (*Protective Groups in Organic Chemistry*, Wiley and Sons, 1991).

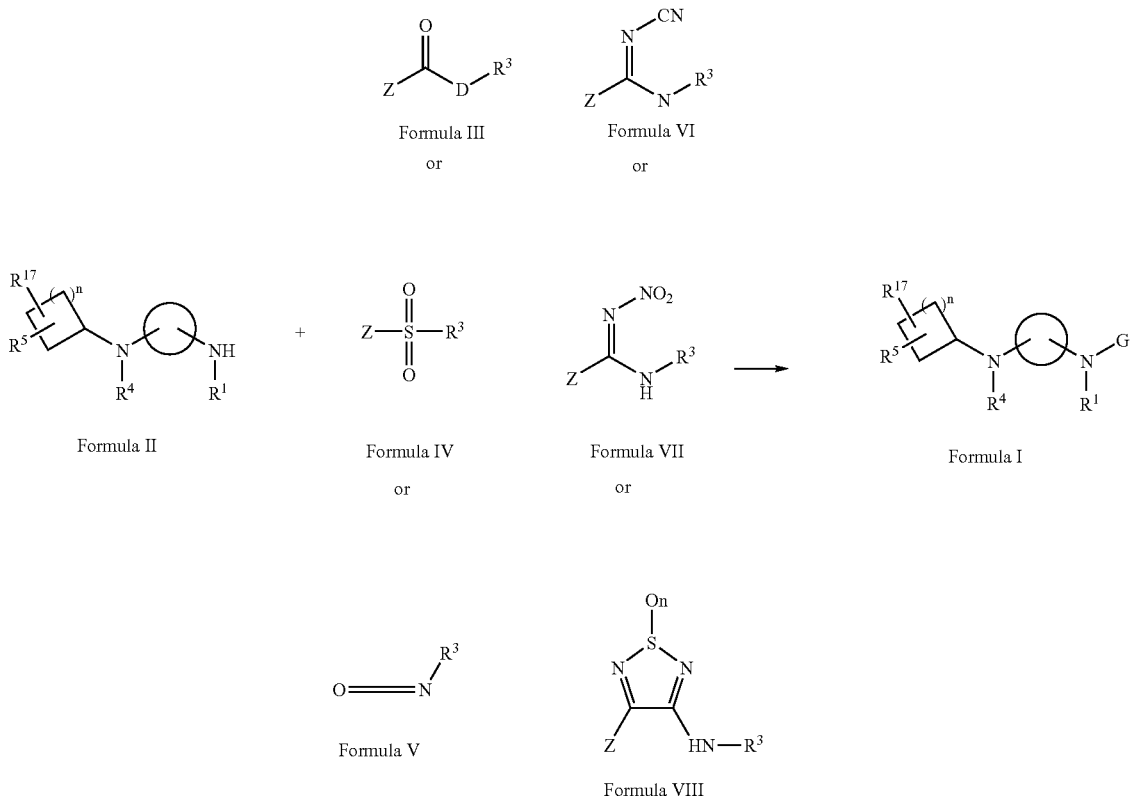

Compounds of Formula I may be prepared as shown in Scheme 1. Compounds in which D is a bond, O or NR$^1$ may be synthesized by reacting Formula II with Formula III, wherein Z is a good leaving such as but not limited to Cl, Br, or imidazole, in the presence of a base such as, but not limited to, triethylamine or pyridine. Alternatively, Formula II may be reacted with an isocyanate of Formula V to provide compounds of Formula I where G is CONHR$^3$. Alternatively, Formula II may be reacted with Formula IV, wherein Z is a good leaving group such as but not limited to Cl, Br, or imidazole, in the presence of a base such as, but not limited to, triethylamine or pyridine to provide compounds of Formula I where G is SO$_2$R$^3$. Alternatively, Formula II may be reacted with Formulas VI, VII, or VIII wherein Z is a good leaving group such as but not limited to ethoxide, phenoxide, or methylsulfide to provide compounds of Formula I according to procedures described in Hoffman, et. al. *J. Med. Chem.* 1983, 26, 140 and references therein.

Scheme 2

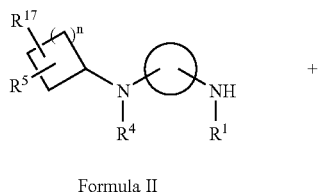

Formula II

+

Cl—[heterocycle with Z$^1$, Z$^2$]

Pd$_2$(dba)$_3$
―――――――→
Binap, NaOt-Bu, toluene, 85° C.

[Formula I structure]

Formula I

Alternatively, compounds of Formula I can be synthesized by coupling compounds of Formula II with halogenated heterocycles of Formula IX as described in Scheme 2. It is understood that the chemistry is shown for only one heterocycle and that similar transformations may be preformed on other halogenated heterocycles. This procedure essentially follows the general procedures of Hong, Y. et. al., *Tet. Lett.* 1997, 38, 5607 and references therein, with minor modification depending on the Formula IX which should be readily recognized by one skilled in the art. The reaction can be preformed in an inert solvent such as, but not limited to, toluene at room temperature to the reflux temperature of the solvent with a Pd-catalyst such as Pd2(dba)$_3$ and a base such as sodium t-butoxide. The halogenated heterocycles that are not commercial available can be synthesized by methods known in the art and are exemplified by, but not limited to, Zou. R., *J. Med Chem.* 1997, 40, 802.

Scheme 3

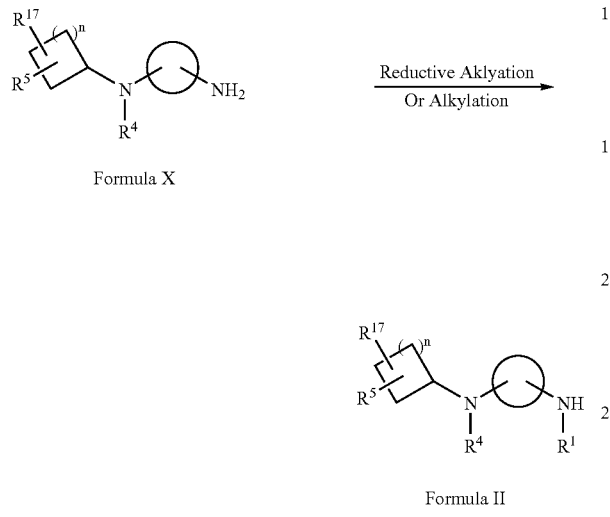

Formula X

Reductive Aklyation Or Alkylation

Formula II

Compounds of Formula II, where R[1] is not hydrogen, may be prepared by procedures depicted in Scheme 3. Reductive alkylation of Formula X with an aldehyde or ketone is carried out under conditions known in the art, for example, catalytic hydrogenation with hydrogen in the presence of palladium or platinum or with reducing agents such as sodium triacetoxyborohydride. Alternatively, a similar transformation can be accomplished with an alkylating agent R[1]Z where Z is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent.

Scheme 4

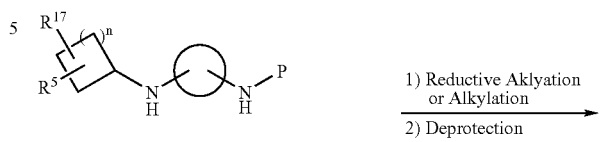

Formula XI

1) Reductive Aklyation or Alkylation
2) Deprotection

Formula X

Compounds of Formula X, where R[4] is not hydrogen, may be prepared by procedures depicted in Scheme 4. Reductive alkylation of Formula XI with an aldehyde or ketone is carried out under conditions known in the art, for example, catalytic hydrogenation with hydrogen in the presence of palladium or platinum or with reducing agents such as sodium triacetoxyborohydride. Alternatively, a similar transformation can be accomplished with an alkylating agent R[4]Z where Z is a halide (halide=Cl, Br, I), mesylate, tosylate, triflate, etc. in the presence of a base such as triethylamine, pyridine, etc. in acetonitrile, DMF, DMSO, etc. at room temperature to reflux temperature of the solvent. The protecting group (P) can then be removed using the appropriate reagents, well familiar to one skilled in the art, and typical examples may be found in Greene, T and Wuts, P. G. M., *Protecting Groups in Organic Synthesis*, John Wiley & Sons, Inc., New York, N.Y., 1991 and references therein, to provide intermediates of Formula X.

Scheme 5

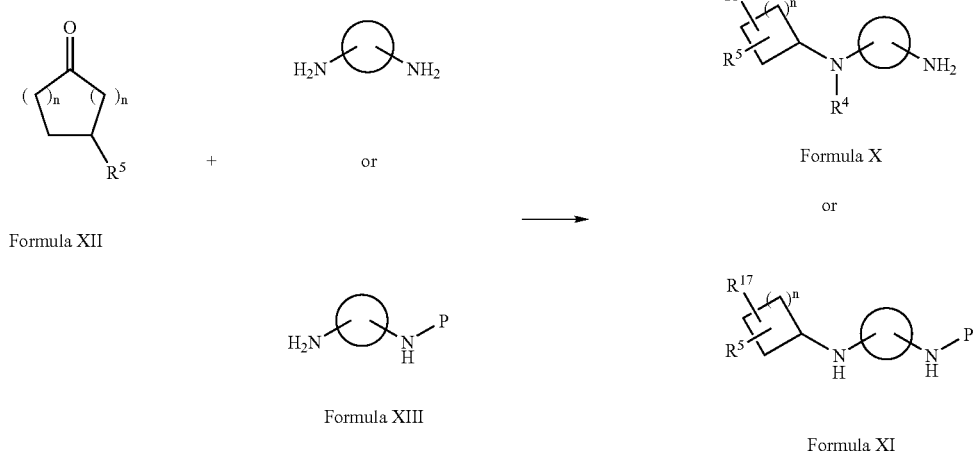

Formula XII

Formula XIII

Formula X or

Formula XI

Compounds of Formula X, where $R^4$ is hydrogen, or Formula XI may be prepared by procedures depicted in Scheme 5. Reductive alkylation of Formula XIII with a cyclic ketone of Formula XII can be carried out under conditions known in the art, for example, catalytic hydrogenation with hydrogen in the presence of palladium or platinum or with reducing agents such as sodium triacetoxyborohydride. Compounds of Formula XIII that are not commercially available can be synthesized by methods known in the art and are exemplified by, but not limited to, Guan et. al., *Synlett* 1999, 426, Skarzewski and Gupta *Tetrahedron: Asymmetry*, 1997, 8, 1861, Bitha, and Lin, *J. Heterocycl. Chem.* 1988, 25, 1035, Ohba et. al., *Agric. Biol. Chem.* 1974, 38, 2431, and Toftlund, and Pedersen, *Acta Chem. Scand.*, 1972, 26, 4019.

EXAMPLES

Example 1

Preparation of N-(3-acetylphenyl)-N'-[(2R)-2-[[cis-4-[(4-fluorophenyl)methyl]-1-cyclohexyl]amino]-(1R)-1-cyclohexyl]urea hydrochloride Part A. Preparation of 8-[(4-fluorophenyl)methylene]-1,4-dioxaspiro[4.5]decane To a stirring solution of 4-fluorophenylmethyl triphenylphosphonium chloride (39 g, 96 mmol, Lancaster) in 500 mL of dry THF at −78° C. was added 1 M potassium t-butoxide in THF (106 mL, 106 mmol, Aldrich). The

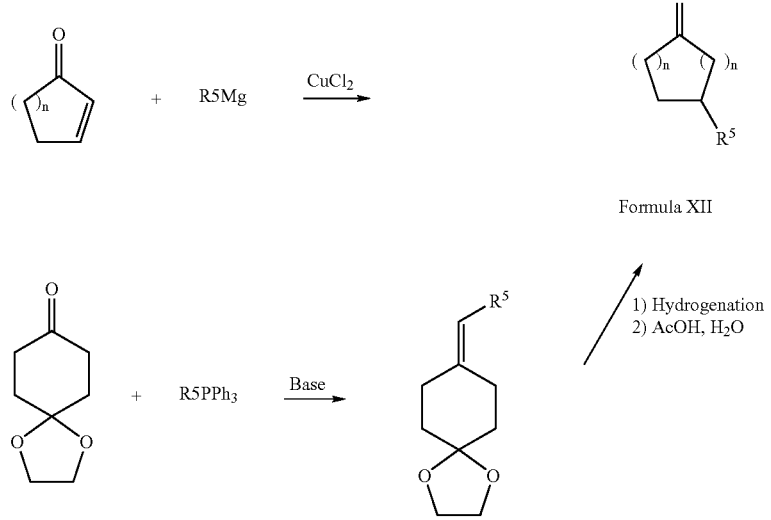

Scheme 6

Formula XII

Compounds of Formula XII may be prepared by procedures depicted in Scheme 6. This procedure essentially follows the general protocols of Mitra and Joshi, *Synth. Commun.*, (1988), 18, 2259 and references therein, with minor modification depending on $R^5$ which should be readily recognized by one skilled in the art. The cycloalkenones can be treated with grinard reagents in the presence of copper chloride to incorporate $R^5$ to produce compounds of Formula XII. Alternatively, monoprotected cyclic diketones can be treated under wittig reaction conditions, well known to one skilled in the art, and then hydrogenated and deprotected to produce compounds of Formula XII. Other methods for producing compounds of Formula XII can be found in the reference Lednicer et. al., *J. Med. Chem.* 1972, 15, 1239.

The compounds of this invention and their preparation can be understood further by the following working examples, which do not constitute a limitation of the invention.

reaction was stirred for 30 min and then warmed to 0° C. The reaction was stirred for 30 min and then 1,4-cyclohexanedione mono-ethylene ketal (15.0 g, 96 mmol, Aldrich) was added. After 30 min, the reaction was warmed to room temperature and allowed to stir overnight. The reaction was heated to reflux for 4 h and then cooled to room temperature. The reaction was quenched with saturated ammonium chloride (500 mL) and ethyl acetate (500 mL). The organic layer was separated, washed with brine, dried over sodium sulfate, and conc in vacuo to a white solid. The solid was purified by flash chromatography (SiO2, 19:1 hexanes:ethyl acetate) to yield 18.9 g of a colorless oil. MS (ESI) 251 (M+H).

Part B: Preparation of 8-[(4-fluorophenyl)methyl]-1,4-dioxaspiro[4.5]decane

To a stirring degassed solution of 8-[(4-fluorophenyl)methylene]-1,4-dioxaspiro[4.5]decane (18.9 g, 76 mmol) and 10% palladium on carbon (3.8 g, Aldrich) in 500 mL of ethyl acetate was added 40 psi of hydrogen gas. The reaction was stirred for 2.5 h and then filtered through a pad of silica gel. The silica gel was washed with ethyl acetate (300 mL). The organic layers were combined and conc in vacuo to a colorless oil yielding 18.0 g. MS (ESI) 253 (M+H).

Part C. Preparation of 4-[(4-fluorophenyl)methyl]-cyclohexanone

To a stirring solution of 8-[(4-fluorophenyl)methyl]-1,4-dioxaspiro[4.5]decane (18 g, 72 mmol) in 100 mL of THF was added 1 M hydrogen chloride in water (70 mL) followed by conc hydrogen chloride (50 mL). The reaction was heated to reflux for 5 h and then cooled to room temperature. The reaction was conc in vacuo to 120 mL and then extracted with ethyl acetate (3×100 mL). The organic layers were combined, washed with sat sodium bicarbonate, brine, dried over sodium sulfate, and conc in vacuo to a colorless oil. The oil was purified by flash chromatography (SiO2, 10:1 hexanes:ethyl acetate) to yield 9.6 g of a colorless oil. MS (ESI) 207 (M+H).

Part D. Preparation (2R)-2-[[cis-4-[(4-fluorophenyl) methyl]-1-cyclohexyl]amino]-(1R)-1-aminocyclohexane ditrifluoroacetate and (2R)-2-[[trans-4-[(4-fluorophenyl)methyl]-1-cyclohexyl]amino]-(1R)-1-aminocyclohexane ditrifluoroacetate To a stirring solution of 4-[(4-fluorophenyl)methyl]-cyclohexanone (110 mg, 0.53 mmol) and (1R,2R)-1,2-diaminocyclohexane (76 mg, 0.66 mmol, Aldrich) in 10 mL of methylene chloride was added sodium triacetoxyborohydride (212 mg, 1 mmol, Aldrich). The reaction was stirred for 16 h and then quenched by the addition of 2N sodium hydroxide (5 mL). The reaction was extracted with ethyl acetate (3×10 mL). The organic layers were combined, dried over magnesium sulfate, and conc in vacuo to a yellow oil. The oil was purified by HPLC (C18, 90% water with 0.1% TFA/10% acetonitrile to 10% water with 0.1% TFA/90% acetonitrile) to yield 210 g of a white solid. MS (ESI) 305 (M-2TFA).

Part E. Preparation N-(3-acetylphenyl)-N'-[(2R)-2-[[cis-4-[(4-fluorophenyl)methyl]-1-cyclohexyl] amino]-(1R)-1-cyclohexyl]urea hydrochloride To a stirring solution of (2R)-2-[[cis-4-[(4-fluorophenyl) methyl]-1-cyclohexyl]amino]-(1R)-1-amino-cyclohexane ditrifluoroacetate and (2R)-2-[[trans-4-[(4-fluorophenyl)methyl]-1-cyclohexyl]amino]-(1R)-1-aminocyclohexane ditrifluoroacetate (80 mg, 0.15 mmol) and triethylamine (61 mg, 0.6 mmol, Aldrich) in 3 mL of dry THF was added 3-acetylphenyl isocyanate (24 mg, 0.15 mmol, Aldrich). The reaction was stirred for 30 min and then quenched by the addition of methanol (1 mL). The reaction was conc in vacuo to a yellow oil. The oil was purified radial chromatography (SiO2, ethyl acetate with 3% triethylamine) to yield a colorless oil. The oil was dissolved in ethyl ether and treated with 1 equivalent of 1M hydrochloric acid in ethyl ether. The solution was conc in vacuo to a white solid. The solid was dissolved in 1:1 acetonitrile and water and then lyophilized to yield 33 mg of a white solid. MS (ESI) 466 (M-Cl).

Example 2

Preparation of N-(3-acetylphenyl)-N'-[(2R)-2-[[trans-4-[(4-fluorophenyl)methyl]-1-cyclohexyl] amino]-(1R)-1-cyclohexyl]urea hydrochloride The compound was isolated from the purification step of Example 1, Part E and converted to the HCl salt according to procedures in Step E. MS (ESI) 466 (M-Cl).

Example 3

Preparation of N-(3-cyanophenyl)-N'-[(2R)-2-[[trans-4-[(4-fluorophenyl)methyl]-1-cyclohexyl] amino]-(1R)-1-cyclohexyl]urea trifluoroacetate and N-(3-cyanophenyl)-N'-[(2R)-2-[[cis-4-[(4-fluorophenyl)methyl]-1-cyclohexyl]amino]-(1R)-1-cyclohexyl]urea trifluoroacetate Prepared according to procedures described in Example 1 with modification at Step E. The compound was purified by HPLC (C18, 90% water with 0.1% TFA/10% acetonitrile to 10% water with 0.1% TFA/90% acetonitrile) to yield a white solid. MS (ESI) 449 (M-TFA).

Example 4

Preparation of N-(3-cyanophenyl)-N'-[(2S)-2-[[trans-4-[(4-fluorophenyl)methyl]-1-cyclohexyl] amino]-(1S)-1-cyclohexyl]urea trifluoroacetate and N-(3-cyanophenyl)-N'-[(2S)-2-[[cis-4-[(4-fluorophenyl)methyl]-1-cyclohexyl]amino]-(1S)-1-cyclohexyl]urea trifluoroacetate Prepared according to procedures described in Example 3 with modification at Step E. MS (ESI) 449 (M-TFA).

Example 5

Preparation of N-(3-acetylphenyl)-N'-[(2S)-2-[[trans-4-[(4-fluorophenyl)methyl]-1-cyclohexyl] amino]-(1S)-1-cyclohexyl]urea trifluoroacetate and N-(3-acetylphenyl)-N'-[(2S)-2-[[cis-4-[(4-fluorophenyl)methyl]-1-cyclohexyl]amino]-(1S)-1-cyclohexyl]urea trifluoroacetate Prepared according to procedures described in Example 3 with modification at Step E. MS (ESI) 449 (M-TFA).

Example 6

Preparation of N-(3-acetylphenyl)-N'-[(2R)-2-[[(3R)-3-[(4-fluorophenyl)methyl]-(1R)-1-cyclohexyl]amino]-(1R)-1-cyclohexyl]urea Prepared according to procedures described in Example 1 with modification at Step A in which 3-(4-fluorophenyl)-methylcyclohexanone, prepared according to procedures published by Mitra and Joshi, *Synth. Comm.* 1988, 18, 2559 and separated into the S and R enantiomers by HPLC (Chiralpak AD, ethanol), was substituted for 4-(4-fluorophenyl)methylcyclohexanone and the products were not converted to the hydrochloride salts. The. MS (ESI) 466 (M+H).

Example 7

Preparation of N-(3-acetylphenyl)-N'-[(2R)-2-[[(3R)-3-[(4-fluorophenyl)methyl]-(1S)-1-cyclohexyl]amino]-(1R)-1-cyclohexyl]urea Prepared according to procedures described in Example 6. MS (ESI) 466 (M+H).

Example 8

Preparation of N-(3-acetylphenyl)-N'-[(2R)-2-[[(3S)-3-[(4-fluorophenyl)methyl]-(1R)-1-cyclohexyl]amino]-(1R)-1-cyclohexyl]urea Prepared according to procedures described in Example 6. MS (ESI) 466 (M+H).

Example 9

Preparation of N-(3-acetylphenyl)-N'-[(2R)-2-[[(3S)-3-[(4-fluorophenyl)methyl]-(1S)-1-cyclohexyl]amino]-(1R)-1-cyclohexyl]urea Prepared according to procedures described in Example 6. MS (ESI) 466 (M+H).

Example 10

Preparation of N-(4-fluorophenyl)-N'-[(2R)-2-[[(3R)-3-[(4-fluorophenyl)methyl]-(1R)-1-cyclohexyl]amino]-(1R)-1-cyclohexyl]urea Prepared according to procedures described in Example 6. MS (ESI) 442 (M+H).

Example 11

Preparation of N-(4-fluorophenyl)-N'-[(2R)-2-[[(3R)-3-[(4-fluorophenyl)methyl]-(1S)-1-cyclohexyl]amino]-(1R)-1-cyclohexyl]urea Prepared according to procedures described in Example 6. MS (ESI) 442 (M+H).

Example 12

Preparation of N-(4-fluorophenyl)-N'-[(2R)-2-[[(3S)-3-[(4-fluorophenyl)methyl]-(1R)-1-cyclohexyl]amino]-(1R)-1-cyclohexyl]urea Prepared according to procedures described in Example 6. MS (ESI) 442 (M+H).

Example 13

Preparation of N-(4-fluorophenyl)-N'-[(2R)-2-[[(3S)-3-[(4-fluorophenyl)methyl]-(1S)-1-cyclohexyl]amino]-(1R)-1-cyclohexyl]urea Prepared according to procedures described in Example 6. MS (ESI) 442 (M+H).

Example 14

Preparation of N-(3-acetylphenyl)-N'-((3S,4S)-4-{[4-(4-fluorobenzyl)cyclohexyl]amino}tetrahydro-3-furanyl)urea hydrochloride Part A. Preparation of (3S,4S)-3-aminotetrahydrofuran-4-yl carbamic Acid tert-Butyl ester A flame-dried round bottom flask under nitrogen was charged with dry tetrahydrofuran (17 mL) and ((3S,4S)-tetrahydro-3,4-furandiamine (170 mg, 1.70 mmol) prepared according to the procedures of Skarzewski, J., et al. *Tetrahedron: Asymmetry* 1997, 8 (11), 1861. The solution was cooled to −78° C., and 2.5 M n-butyl lithium in hexanes (700 µL, 1.75 mmol) was added. The resulting cloudy white suspension was warmed to 23° C., and the suspension became orange. After 10 min, tert-butyl dicarbonate (371 mg, 1.70 mmol) was added in one portion. An additional 100 mg-portion of tert-butyl dicarbonate was added after 10 min. The reaction was then poured into saturated aqueous sodium chloride (50 mL), and the aqueous layer was washed with ethyl acetate (4×20 mL). The combined organic layers were dried over sodium sulfate, concentrated, and the resulting residue was purified by flash chromatography (5–10% methanol in dichloromethane) to yield the desired amine (90 mg, 26%) as a yellow oil. MS (ESI) 203 (M+H).

Part B. Preparation of tert-butyl(3S,4S)-4-{[4-(4-fluorobenzyl)cyclohexyl]amino}tetrahydro-3-furanylcarbamate To a flame-dried round bottom flask under nitrogen containing (3S,4S)-3-aminotetrahydrofuran-4-yl carbamic acid tert-butyl ester (90 mg, 0.45 mmol) and 4-(4-fluorobenzyl)cyclohexanone (87 mg, 0.42 mmol) in 1,2-dichloroethane (6 mL) was added sodium triacetoxyborohydride (191 mg, 0.90 mmol). The resulting yellow mixture was stirred for 15 min and was then poured into 1N aqueous hydrogen chloride (50 mL). The aqueous layer was basified with 50% aqueous sodium hydroxide and washed with ethyl acetate (4×20 mL). The combined organic layers were dried over sodium sulfate, concentrated, and the resulting residue was purified by flash chromatography (5% methanol in dichloromethane) to yield the desired carbamic acid tert-butyl ester (94 mg, 53%) as a yellow oil. MS (ESI) 393 (M+H).

Part C. Preparation of (3S,4S)-$N^3$-[4-(4-fluorobenzyl)cyclohexyl]tetrahydro-3,4-furandiamine dihydrochloride To tert-butyl(3S,4S)-4-{[4-(4-fluorobenzyl)cyclohexyl]amino}tetrahydro-3-furanylcarbamate (94 mg, 0.24 mmol) was added 4 M hydrogen chloride in dioxane (5 mL). Methanol (0.5 mL) was added to dissolve the resulting precipitate. The resulting solution was concentrated after monitoring by electrospray mass spectrometry showed the reaction to be complete. Concentration afforded the desired dihydrochloride (88 mg, 100%) as a white solid. MS (ESI) 293 (M-HCl$_2$).

Part D. Preparation of N-(3-acetylphenyl)-N'-((3S,4S)-4-{[4-(4-fluorobenzyl)cyclohexyl]amino}tetrahydro-3-furanyl)urea To a stirring solution of (3S,4S)-$N^3$-[4-(4-fluorobenzyl)cyclohexyl]tetrahydro-3,4-furandiamine dihydrochloride (20 mg, 0.055 mmol) and triethylamine (100 µL, 0.72 mmol) in dichloromethane (1 mL) was added 3-acetylphenyl isocyanate (7.1 mg, 0.050 mmol). The resulting solution was immediately concentrated, and the resulting residue was purified by flash column chromatography (100% ethyl acetate then 5% triethylamine in ethyl acetate then 10% methanol in ethylacetate containing 5% triethylamine) to yield the desired urea (15 mg, 60%) as an oily white solid. MS (ESI) 454 (M+H).

Part E. Preparation of N-(3-acetylphenyl)-N'-((3S, 4S)-4-{[4-(4-fluorobenzyl)cyclohexyl] amino}tetrahydro-3-furanyl)urea hydrochloride To a stirring solution of N-(3-acetylphenyl)-N'-(3S,4S)-4-{[4-(4-fluorobenzyl)cyclohexyl]amino}tetrahydro-3-furanyl)urea (14 mg, 0.030 mmol) in dichloromethane (1 mL) was added 1.0 M hydrogen chloride in ether (300 µL, 0.030 mmol). After 5 min, the resulting solution was concentrated and the residue lyopholized to afford the desired hydrochloride (15 mg, 100%) as a white solid. MS (ESI) 454 (M-Cl).

Example 15

Preparation of N-(3-acetylphenyl)-N'-({(2S)-1-[cis-4-(4-fluorobenzyl)cyclohexyl]pyrrolidinyl}methyl) urea Part A. Preparation of {(2S)-1-[cis-4-(4-fluorobenzyl)cyclohexyl]pyrrolidinyl}methanol and {(2S)-1-[trans-4-(4-fluorobenzyl)cyclohexyl] pyrrolidinyl}methanol To a stirring solution of 4-fluorophenylmethyl-cyclohexanone (300 mg, 1.45 mmol, 1 eq.) and (S)-2-pyrrolidinemethanol (0.14 ml, 1.45 mmol, Aldrich) in 2 ml of 1,2-dichloroethane at 25° C. was added sodium triacetoxyborohydride (462 mg, 2.18 mmol, Aldrich). The reaction was stirred for 5 hours then worked up by adding 10 ml of 1N NaOH then extracting 3 times with chloroform. The organic was combined, dried over magnesium sulfate, and concentrated in vacuo to obtain 400 mg of an oil as mixture of diastereomeric products. MS (ESI) detects 292 (M+H).

Part B. Preparation of (2S)-2-(chloromethyl)-1-[cis-4-(4-fluorobenzyl)cyclohexyl]pyrrolidine To a stirring solution of {(2S)-1-[cis-4-(4-fluorobenzyl) cyclohexyl]pyrrolidinyl}methanol and {(2S)-1-[trans-4-(4-fluorobenzyl)cyclohexyl]pyrrolidinyl}methanol (390 mg, 1.34 mmol) in 5 ml of methylene chloride at 25° C. under $N_2$ was added pyridine (0.22 ml, 2.75 mmol, EM Science) followed by p-toluenesulfonyl chloride (288 mg, 1.51 mmol, Aldrich). Worked up after 16 hours by adding ethyl acetate then rinsing 3 times with sat'd sodium bicarbonate followed by 1 time time with brine. The organic was dried over magnesium sulfate, and concentrated in vacuo to obtain an oil which was purified over silica gel in 100% ethyl acetate to yield 87 mg of product. MS (ESI) detects 310 (M+H). The other isomer was isolated and used for example 16.

Part C. Preparation of (2S)-2-(azidomethyl)-1-[cis-4-(4-fluorobenzyl)cyclohexyl]pyrrolidine To a stirring solution of (2S)-2-(chloromethyl)-1-[cis-4-(4-fluorobenzyl)cyclohexyl]pyrrolidine in 2 ml of DMSO (Aldrich) at 25° C. under $N_2$ was added sodium azide (28 mg, 2.90 mmol, Aldrich). The reaction was heated at 50° C. for 16 hours. Worked up by adding ethyl acetate then rinsing 5 times with H2O. The organic was dried over magnesium sulfate, and concentrated in vacuo to obtain 45 mg of an amber oil as product. MS (ESI) detects 317 (M+H).

Part D. Preparation of {(2S)-1-[cis-4-(4-fluorobenzyl)cyclohexyl]pyrrolidinyl}methanamine (2S)-2-(azidomethyl)-1-[cis-4-(4-fluorobenzyl)cyclohexyl]pyrrolidine (45 mg), 10% Pd/C (10 mg, Aldrich) and 5 ml of methanol were hydrogenated for 16 hours at 50 PSI. The reaction was filtered through fiberglass filter paper under nitrogen. The filtrate was stripped to yield 58 mg of an amber oil as product. MS (ESI) detects 291 (M+H).

Part E. Preparation of N-(3-acetylphenyl)-N'-({(2S)-1-[cis-4-(4-fluorobenzyl)cyclohexyl] pyrrolidinyl}methyl)urea To a stirring solution of {(2S)-1-[cis-4-(4-fluorobenzyl) cyclohexyl]pyrrolidinyl}methanamine (58 mg, 2 mmol) in 2 ml of THF at 25° C. under $N_2$ was added 3 acetylphenyl isocyanate (32 mg, 2 mmol Aldrich). Worked up after 4 hours by stripping off the THF then purifying over silica gel in 100% ethyl acetate followed by 4:1 chloroform/methanol. Obtained 11 mg of a white foam as product. MS (ESI) detects 452 (M+H).

Example 16

Preparation of N-(3-acetylphenyl)-N'-({(2S)-1-[trans-4-(4-fluorobenzyl)cyclohexyl] pyrrolidinyl}methyl)urea Prepared according to procedures described in Example 15. MS (ESI) detects 452 (M+H).

Example 17

Preparation of N-(3-acetylphenyl)-N'-({(2R)-1-[cis-4-(4-fluorobenzyl)cyclohexyl]pyrrolidinyl}methyl) urea Prepared according to procedures described in Example 15 except starting with (R)-2-pyrrolidinemethanol. MS (ESI) detects 452 (M+H).

Example 18

Preparation of N-(3-acetylphenyl)-N'-({(2R)-1-[trans-4-(4-fluorobenzyl)cyclohexyl] pyrrolidinyl}methyl)urea Prepared according to procedures described in Example 15 except starting with (R)-2-pyrrolidinemethanol. MS (ESI) detects 452 (M+H).

Example 19

Preparation of N-(3-acetylphenyl)-N'-{(3R)-1-[cis-4-(4-fluorobenzyl)cyclohexyl]pyrrolidinyl}urea Prepared according to procedures described in Example 14 steps b-d except starting with (3R)-(+)-3-(tert-butoxycarbonylamino)pyrrolidine. MS (ESI) detects 438 (M+H).

Example 20

Preparation of N-(3-acetylphenyl)-N'-{(3R)-1-[trans-4-(4-fluorobenzyl)cyclohexyl]pyrrolidinyl}urea Prepared according to procedures described in Example 14 steps b–d except starting with (3R)-(+)-3-(tert-butoxycarbonylamino)pyrrolidine. MS (ESI) detects 438 (M+H).

Example 21

Preparation of N-(3-acetylphenyl)-N'-{(3S)-1-[cis-4-(4-fluorobenzyl)cyclohexyl]pyrrolidinyl}urea Prepared according to procedures described in Example 14 steps b–d except starting with (3S)-(+)-3-(tert-butoxycarbonylamino)pyrrolidine. MS (ESI) detects 438 (M+H).

Example 22

Preparation of N-(3-acetylphenyl)-N'-{(3S)-1-[trans-4-(4-fluorobenzyl)cyclohexyl]pyrrolidinyl}urea Prepared according to procedures described in Example 14 steps b–d except starting with (3S)-(+)-3-(tert-butoxycarbonylamino)pyrrolidine. MS (ESI) detects 438 (M+H).

The following table contains representative examples of the present invention. Each entry in the table is intended to be paired with each formulae at the start of the table. For example, entry 1 in Table 1 is intended to be paired with a–r.

TABLE 1

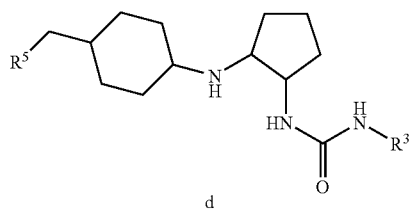

a

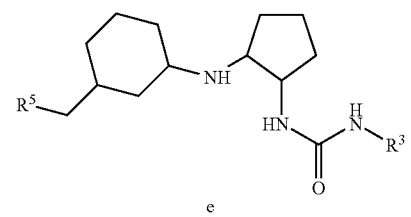

b

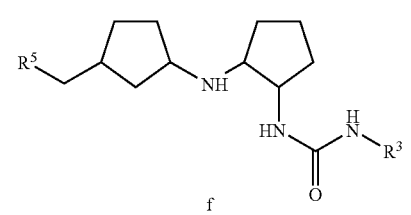

c

TABLE 1-continued

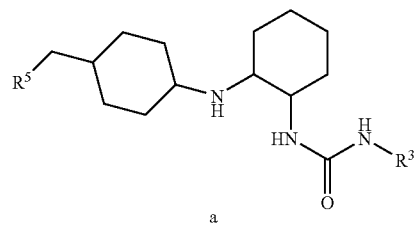

d

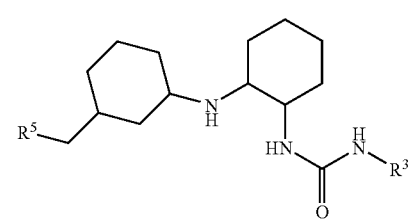

e

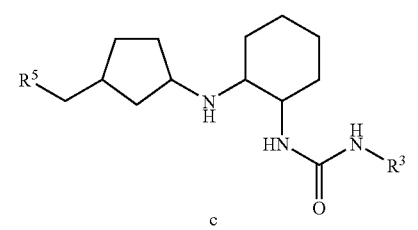

f

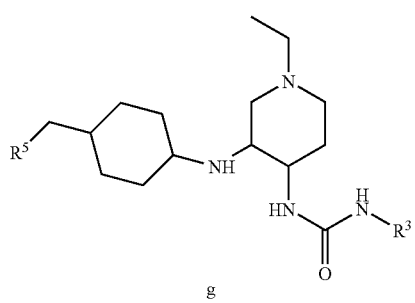

g

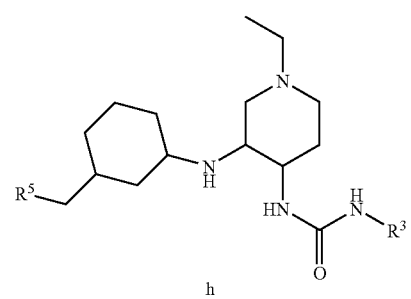

h

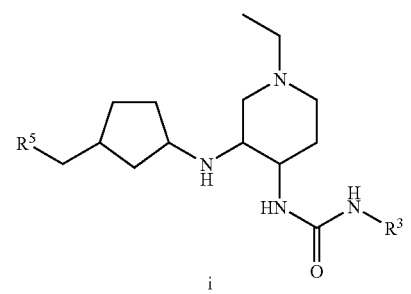

i

TABLE 1-continued

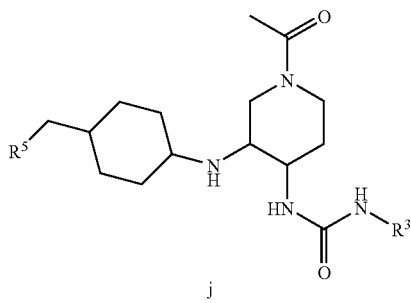
j

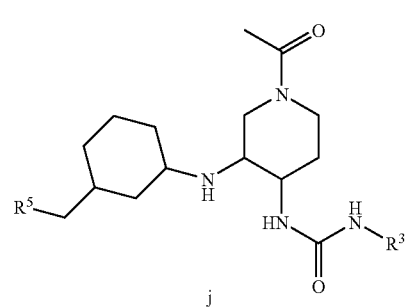
j

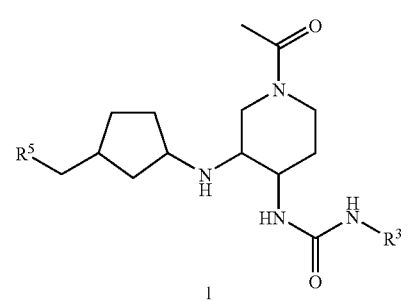
l

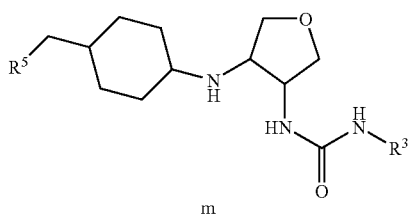
m

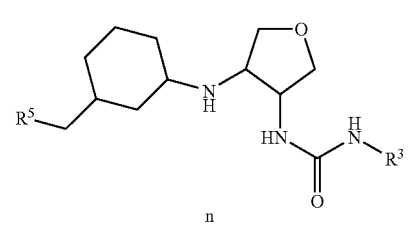
n

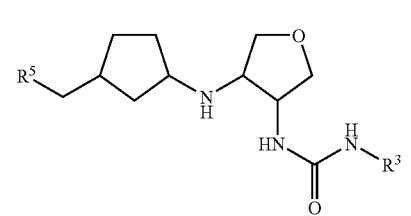
o

TABLE 1-continued

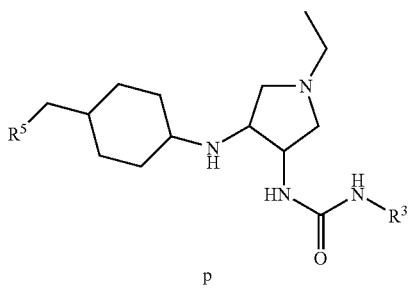
p

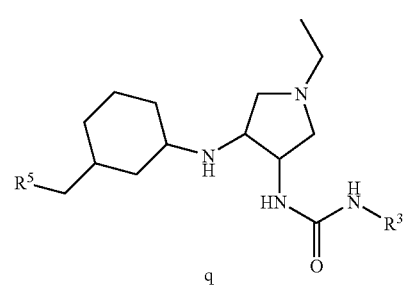
q

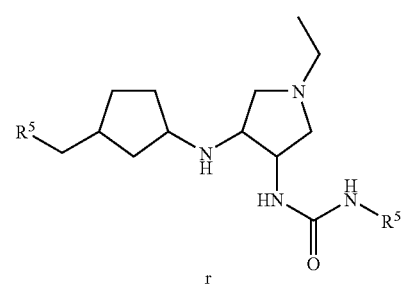
r

| ENTRY | R$^5$ | R$^3$ |
|---|---|---|
| 1 | 4-F—Ph | Ph |
| 2 | 4-F—Ph | 3-CN—Ph |
| 3 | 4-F—Ph | 3-COCH3-Ph |
| 4 | 4-F—Ph | 3-CO2Me—Ph |
| 5 | 4-F—Ph | 3-CO2Et—Ph |
| 6 | 4-F—Ph | 3-CO2H—Ph |
| 7 | 4-F—Ph | 3-CONH2-Ph |
| 8 | 4-F—Ph | 3-CONHMe—Ph |
| 9 | 4-F—Ph | 3-F—Ph |
| 10 | 4-F—Ph | 3-Cl—Ph |
| 11 | 4-F—Ph | 3-Br—Ph |
| 12 | 4-F—Ph | 3-NO2-Ph |
| 13 | 4-F—Ph | 3-NH2-Ph |
| 14 | 4-F—Ph | 3-NHMe-Ph |
| 15 | 4-F—Ph | 3-NMe2-Ph |
| 16 | 4-F—Ph | 3-NHCOCH3-Ph |
| 17 | 4-F—Ph | 3-SO2NH2-Ph |
| 18 | 4-F—Ph | 3-SO2NHMe—Ph |
| 19 | 4-F—Ph | 3-CF3-Ph |
| 20 | 4-F—Ph | 3-OCH3-Ph |
| 21 | 4-F—Ph | 3-OPh—Ph |
| 22 | 4-F—Ph | 3-OCF3-Ph |
| 23 | 4-F—Ph | 3-SCH3-Ph |
| 24 | 4-F—Ph | 3-SOCH3-Ph |
| 25 | 4-F—Ph | 3-SO2CH3-Ph |
| 26 | 4-F—Ph | 3-OH—Ph |
| 27 | 4-F—Ph | 3-CH2OH—Ph |
| 28 | 4-F—Ph | 3-CHOHCH3-Ph |
| 29 | 4-F—Ph | 3-COH(CH3)2-Ph |
| 30 | 4-F—Ph | 3-CHOHPh—Ph |
| 31 | 4-F—Ph | 3-CH3-Ph |
| 32 | 4-F—Ph | 3-C2H5-Ph |
| 33 | 4-F—Ph | 3-iPr—Ph |
| 34 | 4-F—Ph | 3-tBu—Ph |
| 35 | 4-F—Ph | 3-Ph—Ph |

TABLE 1-continued

| | | |
|---|---|---|
| 36 | 4-F—Ph | 3-CH2Ph—Ph |
| 37 | 4-F—Ph | 3-CH2CO2Me—Ph |
| 38 | 4-F—Ph | 3-(1-piperidinyl)-Ph |
| 39 | 4-F—Ph | 3-(1-pyrrolidinyl)-Ph |
| 40 | 4-F—Ph | 3-(2-imidazolyl)-Ph |
| 41 | 4-F—Ph | 3-(1-imidazolyl)-Ph |
| 42 | 4-F—Ph | 3-(2-thiazolyl)-Ph |
| 43 | 4-F—Ph | 3-(3-pyrazolyl)-Ph |
| 44 | 4-F—Ph | 3-(1-pyrazolyl)-Ph |
| 45 | 4-F—Ph | 3-(1-tetrazolyl)-Ph |
| 46 | 4-F—Ph | 3-(5-tetrazolyl)-Ph |
| 47 | 4-F—Ph | 3-(2-pyridyl)-Ph |
| 48 | 4-F—Ph | 3-(2-thienyl)-Ph |
| 49 | 4-F—Ph | 3-(2-furanyl)-Ph |
| 50 | 4-F—Ph | 4-CN—Ph |
| 51 | 4-F—Ph | 4-COCH3-Ph |
| 52 | 4-F—Ph | 4-CO2Me—Ph |
| 53 | 4-F—Ph | 4-CO2Et—Ph |
| 54 | 4-F—Ph | 4-CO2H—Ph |
| 55 | 4-F—Ph | 4-CONH2-Ph |
| 56 | 4-F—Ph | 4-CONHMe—Ph |
| 57 | 4-F—Ph | 4-CONHPh—Ph |
| 58 | 4-F—Ph | 4-NHCONH2-Ph |
| 59 | 4-F—Ph | 4-F—Ph |
| 60 | 4-F—Ph | 4-Cl—Ph |
| 61 | 4-F—Ph | 4-Br—Ph |
| 62 | 4-F—Ph | 4-NO2-Ph |
| 63 | 4-F—Ph | 4-NH2-Ph |
| 64 | 4-F—Ph | 4-NHMe—Ph |
| 65 | 4-F—Ph | 4-NMe2-Ph |
| 66 | 4-F—Ph | 4-NHCOCH3-Ph |
| 67 | 4-F—Ph | 4-SO2NH2-Ph |
| 68 | 4-F—Ph | 4-SO2NHMe—Ph |
| 69 | 4-F—Ph | 4-CF3-Ph |
| 70 | 4-F—Ph | 4-OCH3-Ph |
| 71 | 4-F—Ph | 4-OPh—Ph |
| 72 | 4-F—Ph | 4-OCF3-Ph |
| 73 | 4-F—Ph | 4-SCH3-Ph |
| 74 | 4-F—Ph | 4-SOCH3-Ph |
| 75 | 4-F—Ph | 4-SO2CH3-Ph |
| 76 | 4-F—Ph | 4-OH—Ph |
| 77 | 4-F—Ph | 4-CH2OH—Ph |
| 78 | 4-F—Ph | 4-CHOHCH3-Ph |
| 79 | 4-F—Ph | 4-COH(CH3)2-Ph |
| 80 | 4-F—Ph | 4-CH3-Ph |
| 81 | 4-F—Ph | 4-C2H5-Ph |
| 82 | 4-F—Ph | 4-iPr—Ph |
| 83 | 4-F—Ph | 4-tBu—Ph |
| 84 | 4-F—Ph | 4-Ph—Ph |
| 85 | 4-F—Ph | 4-CH2Ph—Ph |
| 86 | 4-F—Ph | 4-CH2CO2Me—Ph |
| 87 | 4-F—Ph | 4-(1-piperidinyl)-Ph |
| 88 | 4-F—Ph | 4-(1-pyrrolidinyl)-Ph |
| 89 | 4-F—Ph | 4-(2-imidazolyl)-Ph |
| 90 | 4-F—Ph | 4-(1-imidazolyl)-Ph |
| 91 | 4-F—Ph | 4-(2-thiazolyl)-Ph |
| 92 | 4-F—Ph | 4-(3-pyrazolyl)-Ph |
| 93 | 4-F—Ph | 4-(1-pyrazolyl)-Ph |
| 94 | 4-F—Ph | 4-(1-tetrazolyl)-Ph |
| 95 | 4-F—Ph | 4-(5-tetrazolyl)-Ph |
| 96 | 4-F—Ph | 4-(2-pyridyl)-Ph |
| 97 | 4-F—Ph | 4-(2-thienyl)-Ph |
| 98 | 4-F—Ph | 4-(2-furanyl)-Ph |
| 99 | 4-F—Ph | 2-CN—Ph |
| 100 | 4-F—Ph | 2-COCH3-Ph |
| 101 | 4-F—Ph | 2-CO2Me—Ph |
| 102 | 4-F—Ph | 2-CO2Et—Ph |
| 103 | 4-F—Ph | 2-CO2H—Ph |
| 104 | 4-F—Ph | 2-CONH2-Ph |
| 105 | 4-F—Ph | 2-CONHMe—Ph |
| 106 | 4-F—Ph | 2-F—Ph |
| 107 | 4-F—Ph | 2-Cl—Ph |
| 108 | 4-F—Ph | 2-Br—Ph |
| 109 | 4-F—Ph | 2-NO2-Ph |
| 110 | 4-F—Ph | 2-NH2-Ph |
| 111 | 4-F—Ph | 2-NHMe—Ph |
| 112 | 4-F—Ph | 2-NMe2-Ph |
| 113 | 4-F—Ph | 2-NHCOCH3-Ph |
| 114 | 4-F—Ph | 2-SO2NH2-Ph |
| 115 | 4-F—Ph | 2-SO2NHMe—Ph |
| 116 | 4-F—Ph | 2-CF3-Ph |
| 117 | 4-F—Ph | 2-OCH3-Ph |
| 118 | 4-F—Ph | 2-OPh—Ph |
| 119 | 4-F—Ph | 2-OCF3-Ph |
| 120 | 4-F—Ph | 2-SCH3-Ph |
| 121 | 4-F—Ph | 2-SOCH3-Ph |
| 122 | 4-F—Ph | 2-SO2CH3-Ph |
| 123 | 4-F—Ph | 2-OH—Ph |
| 124 | 4-F—Ph | 2-CH2OH—Ph |
| 125 | 4-F—Ph | 2-CHOHCH3-Ph |
| 126 | 4-F—Ph | 2-COH(CH3)2-Ph |
| 127 | 4-F—Ph | 2-CHOHPh—Ph |
| 128 | 4-F—Ph | 2-CH3-Ph |
| 129 | 4-F—Ph | 2-C2H5-Ph |
| 130 | 4-F—Ph | 2-iPr—Ph |
| 131 | 4-F—Ph | 2-tBu—Ph |
| 132 | 4-F—Ph | 2-Ph—Ph |
| 133 | 4-F—Ph | 2-CH2Ph—Ph |
| 134 | 4-F—Ph | 2-CH2CO2Me—Ph |
| 135 | 4-F—Ph | 2-(1-piperidinyl)-Ph |
| 136 | 4-F—Ph | 2-(1-pyrrolidinyl)-Ph |
| 137 | 4-F—Ph | 2-(2-imidazolyl)-Ph |
| 138 | 4-F—Ph | 2-(1-imidazolyl)-Ph |
| 139 | 4-F—Ph | 2-(2-thiazolyl)-Ph |
| 140 | 4-F—Ph | 2-(3-pyrazolyl)-Ph |
| 141 | 4-F—Ph | 2-(1-pyrazolyl)-Ph |
| 142 | 4-F—Ph | 2-(1-tetrazolyl)-Ph |
| 143 | 4-F—Ph | 2-(5-tetrazolyl)-Ph |
| 144 | 4-F—Ph | 2-(2-pyridyl)-Ph |
| 145 | 4-F—Ph | 2-(2-thienyl)-Ph |
| 146 | 4-F—Ph | 2-(2-furanyl)-Ph |
| 147 | 4-F—Ph | 2,4-diF—Ph |
| 148 | 4-F—Ph | 2,5-diF—Ph |
| 149 | 4-F—Ph | 2,6-diF—Ph |
| 150 | 4-F—Ph | 3,4-diF—Ph |
| 151 | 4-F—Ph | 3,5-diF—Ph |
| 152 | 4-F—Ph | 2,4-diCl—Ph |
| 153 | 4-F—Ph | 2,5-diCl—Ph |
| 154 | 4-F—Ph | 2,6-diCl—Ph |
| 155 | 4-F—Ph | 3,4-diCl—Ph |
| 156 | 4-F—Ph | 3,5-diCl—Ph |
| 157 | 4-F—Ph | 3,4-diCF3-Ph |
| 158 | 4-F—Ph | 3,5-diCF3-Ph |
| 159 | 4-F—Ph | 5-Cl-2-MeO—Ph |
| 160 | 4-F—Ph | 5-Cl-2-Me—Ph |
| 161 | 4-F—Ph | 2-F-5-Me—Ph |
| 162 | 4-F—Ph | 2-F-5-NO2-Ph |
| 163 | 4-F—Ph | 3,4-OCH2O—Ph |
| 164 | 4-F—Ph | 3,4-OCH2CH2O—Ph |
| 165 | 4-F—Ph | 2-MeO-4-Me—Ph |
| 166 | 4-F—Ph | 2-MeO-5-Me—Ph |
| 167 | 4-F—Ph | 1-naphthyl |
| 168 | 4-F—Ph | 2-naphthyl |
| 169 | 4-F—Ph | 2-thienyl |
| 170 | 4-F—Ph | 3-thienyl |
| 171 | 4-F—Ph | 2-furanyl |
| 172 | 4-F—Ph | 3-furanyl |
| 173 | 4-F—Ph | 2-pyridyl |
| 174 | 4-F—Ph | 3-pyridyl |
| 175 | 4-F—Ph | 4-pyridyl |
| 176 | 4-F—Ph | 2-indolyl |
| 177 | 4-F—Ph | 3-indolyl |
| 178 | 4-F—Ph | 5-indolyl |
| 179 | 4-F—Ph | 6-indolyl |
| 180 | 4-F—Ph | 3-indazolyl |
| 181 | 4-F—Ph | 5-indazolyl |
| 182 | 4-F—Ph | 6-indazolyl |
| 183 | 4-F—Ph | 2-imidazolyl |
| 184 | 4-F—Ph | 3-pyrazolyl |
| 185 | 4-F—Ph | 2-thiazolyl |
| 186 | 4-F—Ph | 5-tetrazolyl |
| 187 | 4-F—Ph | 2-benzimidazolyl |
| 188 | 4-F—Ph | 5-benzimidazolyl |
| 189 | 4-F—Ph | 2-benzothiazolyl |
| 190 | 4-F—Ph | 5-benzothiazolyl |
| 191 | 4-F—Ph | 2-benzoxazolyl |
| 192 | 4-F—Ph | 5-benzoxazolyl |
| 193 | 2-F—Ph | 3-CN—Ph |

TABLE 1-continued

| | | |
|---|---|---|
| 194 | 2-F—Ph | 3-COCH3-Ph |
| 195 | 2-F—Ph | 3-CO2Me—Ph |
| 196 | 2-F—Ph | 3-CO2Et—Ph |
| 197 | 2-F—Ph | 3-CO2H—Ph |
| 198 | 2-F—Ph | 3-CONH2-Ph |
| 199 | 2-F—Ph | 3-F—Ph |
| 200 | 2-F—Ph | 3-Cl—Ph |
| 201 | 2-F—Ph | 3-NH2-Ph |
| 202 | 2-F—Ph | 3-SO2NH2-Ph |
| 203 | 2-F—Ph | 3-CF3-Ph |
| 204 | 2-F—Ph | 3-OCH3-Ph |
| 205 | 2-F—Ph | 3-OEt—Ph |
| 206 | 2-F—Ph | 3-OCF3-Ph |
| 207 | 2-F—Ph | 3-SO2CH3-Ph |
| 208 | 2-F—Ph | 3-OH—Ph |
| 209 | 2-F—Ph | 3-CH3-Ph |
| 210 | 2-F—Ph | 3-C2H5-Ph |
| 211 | 2-F—Ph | 4-CN—Ph |
| 212 | 2-F—Ph | 4-COCH3-Ph |
| 213 | 2-F—Ph | 4-CO2Me—Ph |
| 214 | 2-F—Ph | 4-CO2Et—Ph |
| 215 | 2-F—Ph | 4-CO2H—Ph |
| 216 | 2-F—Ph | 4-CONH2-Ph |
| 217 | 2-F—Ph | 4-F—Ph |
| 218 | 2-F—Ph | 4-Cl—Ph |
| 219 | 2-F—Ph | 4-NH2-Ph |
| 220 | 2-F—Ph | 4-SO2NH2-Ph |
| 221 | 2-F—Ph | 4-CF3-Ph |
| 222 | 2-F—Ph | 4-OCH3-Ph |
| 223 | 2-F—Ph | 4-OEt—Ph |
| 224 | 2-F—Ph | 4-OCF3-Ph |
| 225 | 2-F—Ph | 4-SO2CH3-Ph |
| 226 | 2-F—Ph | 4-OH—Ph |
| 227 | 2-F—Ph | 4-CH3-Ph |
| 228 | 2-F—Ph | 4-C2H5-Ph |
| 229 | 2-F—Ph | 2,4-diF—Ph |
| 230 | 2-F—Ph | 2,5-diF—Ph |
| 231 | 2-F—Ph | 3,4-diF—Ph |
| 232 | 2-F—Ph | 3,5-diF—Ph |
| 233 | 2-F—Ph | 2,4-diCl—Ph |
| 234 | 2-F—Ph | 2,5-diCl—Ph |
| 235 | 2-F—Ph | 3,4-diCl—Ph |
| 236 | 2-F—Ph | 3,5-diCl—Ph |
| 237 | 2-F—Ph | 3,4-OCH2O—Ph |
| 238 | 2-F—Ph | 3,4-OCH2CH2O—Ph |
| 239 | 2-F—Ph | 2-thienyl |
| 240 | 2-F—Ph | 2-furanyl |
| 241 | 2-F—Ph | 2-pyridyl |
| 242 | 2-F—Ph | 4-pyridyl |
| 243 | 2-F—Ph | 2-imidazolyl |
| 244 | 2-F—Ph | 3-pyrazolyl |
| 245 | 2-F—Ph | 2-thiazolyl |
| 246 | 2-F—Ph | 5-tetrazolyl |
| 247 | 2-F—Ph | 1-adamantyl |
| 248 | 2,4-diF—Ph | 3-CN—Ph |
| 249 | 2,4-diF—Ph | 3-COCH3-Ph |
| 250 | 2,4-diF—Ph | 3-CO2Me—Ph |
| 251 | 2,4-diF—Ph | 3-CO2Et—Ph |
| 252 | 2,4-diF—Ph | 3-CO2H—Ph |
| 253 | 2,4-diF—Ph | 3-CONH2-Ph |
| 254 | 2,4-diF—Ph | 3-F—Ph |
| 255 | 2,4-diF—Ph | 3-Cl—Ph |
| 256 | 2,4-diF—Ph | 3-NH2-Ph |
| 257 | 2,4-diF—Ph | 3-SO2NH2-Ph |
| 258 | 2,4-diF—Ph | 3-CF3-Ph |
| 259 | 2,4-diF—Ph | 3-OCH3-Ph |
| 260 | 2,4-diF—Ph | 3-OEt—Ph |
| 261 | 2,4-diF—Ph | 3-OCF3-Ph |
| 262 | 2,4-diF—Ph | 3-SO2CH3-Ph |
| 263 | 2,4-diF—Ph | 3-OH—Ph |
| 264 | 2,4-diF—Ph | 3-CH3-Ph |
| 265 | 2,4-diF—Ph | 3-C2H5-Ph |
| 266 | 2,4-diF—Ph | 4-CN—Ph |
| 267 | 2,4-diF—Ph | 4-COCH3-Ph |
| 268 | 2,4-diF—Ph | 4-CO2Me—Ph |
| 269 | 2,4-diF—Ph | 4-CO2Et—Ph |
| 270 | 2,4-diF—Ph | 4-CO2H—Ph |
| 271 | 2,4-diF—Ph | 4-CONH2-Ph |
| 272 | 2,4-diF—Ph | 4-F—Ph |
| 273 | 2,4-diF—Ph | 4-Cl—Ph |
| 274 | 2,4-diF—Ph | 4-NH2-Ph |
| 275 | 2,4-diF—Ph | 4-SO2NH2-Ph |
| 276 | 2,4-diF—Ph | 4-CF3-Ph |
| 277 | 2,4-diF—Ph | 4-OCH3-Ph |
| 278 | 2,4-diF—Ph | 4-OEt—Ph |
| 279 | 2,4-diF—Ph | 4-OCF3-Ph |
| 280 | 2,4-diF—Ph | 4-SO2CH3-Ph |
| 281 | 2,4-diF—Ph | 4-OH—Ph |
| 282 | 2,4-diF—Ph | 4-CH3-Ph |
| 283 | 2,4-diF—Ph | 4-C2H5-Ph |
| 284 | 2,4-diF—Ph | 2,4-diF—Ph |
| 285 | 2,4-diF—Ph | 2,5-diF—Ph |
| 286 | 2,4-diF—Ph | 3,4-diF—Ph |
| 287 | 2,4-diF—Ph | 3,5-diF—Ph |
| 288 | 2,4-diF—Ph | 2,4-diCl—Ph |
| 289 | 2,4-diF—Ph | 2,5-diCl—Ph |
| 290 | 2,4-diF—Ph | 3,4-diCl—Ph |
| 291 | 2,4-diF—Ph | 3,5-diCl—Ph |
| 292 | 2,4-diF—Ph | 3,4-OCH2O—Ph |
| 293 | 2,4-diF—Ph | 3,4-OCH2CH2O—Ph |
| 294 | 2,4-diF—Ph | 2-thienyl |
| 295 | 2,4-diF—Ph | 2-furanyl |
| 296 | 2,4-diF—Ph | 2-pyridyl |
| 297 | 2,4-diF—Ph | 4-pyridyl |
| 298 | 2,4-diF—Ph | 2-imidazolyl |
| 299 | 2,4-diF—Ph | 3-pyrazolyl |
| 300 | 2,4-diF—Ph | 2-thiazolyl |
| 301 | 2,4-diF—Ph | 5-tetrazolyl |
| 302 | 4-Cl—Ph | Ph |
| 303 | 4-Cl—Ph | 3-CN—Ph |
| 304 | 4-Cl—Ph | 3-COCH3-Ph |
| 305 | 4-Cl—Ph | 3-CO2Me—Ph |
| 306 | 4-Cl—Ph | 3-CO2Et—Ph |
| 307 | 4-Cl—Ph | 3-CO2H—Ph |
| 308 | 4-Cl—Ph | 3-CONH2-Ph |
| 309 | 4-Cl—Ph | 3-CONHMe—Ph |
| 310 | 4-Cl—Ph | 3-F—Ph |
| 311 | 4-Cl—Ph | 3-Cl—Ph |
| 312 | 4-Cl—Ph | 3-Br—Ph |
| 313 | 4-Cl—Ph | 3-NO2-Ph |
| 314 | 4-Cl—Ph | 3-NH2-Ph |
| 315 | 4-Cl—Ph | 3-NHMe—Ph |
| 316 | 4-Cl—Ph | 3-NMe2-Ph |
| 317 | 4-Cl—Ph | 3-NHCOCH3-Ph |
| 318 | 4-Cl—Ph | 3-SO2NH2-Ph |
| 319 | 4-Cl—Ph | 3-SO2NHMe—Ph |
| 320 | 4-Cl—Ph | 3-CF3-Ph |
| 321 | 4-Cl—Ph | 3-OCH3-Ph |
| 322 | 4-Cl—Ph | 3-OPh—Ph |
| 323 | 4-Cl—Ph | 3-OCF3-Ph |
| 324 | 4-Cl—Ph | 3-SCH3-Ph |
| 325 | 4-Cl—Ph | 3-SOCH3-Ph |
| 326 | 4-Cl—Ph | 3-SO2CH3-Ph |
| 327 | 4-Cl—Ph | 3-OH—Ph |
| 328 | 4-Cl—Ph | 3-CH2OH—Ph |
| 329 | 4-Cl—Ph | 3-CHOHCH3-Ph |
| 330 | 4-Cl—Ph | 3-COH(CH3)2-Ph |
| 331 | 4-Cl—Ph | 3-CHOHPh—Ph |
| 332 | 4-Cl—Ph | 3-CH3-Ph |
| 333 | 4-Cl—Ph | 3-C2H5-Ph |
| 334 | 4-Cl—Ph | 3-iPr—Ph |
| 335 | 4-Cl—Ph | 3-tBu—Ph |
| 336 | 4-Cl—Ph | 3-Ph—Ph |
| 337 | 4-Cl—Ph | 3-CH2Ph—Ph |
| 338 | 4-Cl—Ph | 3-CH2CO2Me—Ph |
| 339 | 4-Cl—Ph | 3-(1-piperidinyl)-Ph |
| 340 | 4-Cl—Ph | 3-(1-pyrrolidinyl)-Ph |
| 341 | 4-Cl—Ph | 3-(2-imidazolyl)-Ph |
| 342 | 4-Cl—Ph | 3-(1-imidazolyl)-Ph |
| 343 | 4-Cl—Ph | 3-(2-thiazolyl)-Ph |
| 344 | 4-Cl—Ph | 3-(3-pyrazolyl)-Ph |
| 345 | 4-Cl—Ph | 3-(1-pyrazolyl)-Ph |
| 346 | 4-Cl—Ph | 3-(1-tetrazolyl)-Ph |
| 347 | 4-Cl—Ph | 3-(5-tetrazolyl)-Ph |
| 348 | 4-Cl—Ph | 3-(2-pyridyl)-Ph |
| 349 | 4-Cl—Ph | 3-(2-thienyl)-Ph |
| 350 | 4-Cl—Ph | 3-(2-furanyl)-Ph |
| 351 | 4-Cl—Ph | 4-CN—Ph |

TABLE 1-continued

| | | |
|---|---|---|
| 352 | 4-Cl—Ph | 4-COCH3-Ph |
| 353 | 4-Cl—Ph | 4-CO2Me-Ph |
| 354 | 4-Cl—Ph | 4-CO2Et—Ph |
| 355 | 4-Cl—Ph | 4-CO2H—Ph |
| 356 | 4-Cl—Ph | 4-CONH2-Ph |
| 357 | 4-Cl—Ph | 4-CONHMe—Ph |
| 358 | 4-Cl—Ph | 4-CONHPh—Ph |
| 359 | 4-Cl—Ph | 4-NHCONH2-Ph |
| 360 | 4-Cl—Ph | 4-F—Ph |
| 361 | 4-Cl—Ph | 4-Cl—Ph |
| 362 | 4-Cl—Ph | 4-Br—Ph |
| 363 | 4-Cl—Ph | 4-NO2-Ph |
| 364 | 4-Cl—Ph | 4-NH2-Ph |
| 365 | 4-Cl—Ph | 4-NHMe—Ph |
| 366 | 4-Cl—Ph | 4-NMe2-Ph |
| 367 | 4-Cl—Ph | 4-NHCOCH3-Ph |
| 368 | 4-Cl—Ph | 4-SO2NH2-Ph |
| 369 | 4-Cl—Ph | 4-SO2NHMe—Ph |
| 370 | 4-Cl—Ph | 4-CF3-Ph |
| 371 | 4-Cl—Ph | 4-OCH3-Ph |
| 372 | 4-Cl—Ph | 4-OPh—Ph |
| 373 | 4-Cl—Ph | 4-OCF3-Ph |
| 374 | 4-Cl—Ph | 4-SCH3-Ph |
| 375 | 4-Cl—Ph | 4-SOCH3-Ph |
| 376 | 4-Cl—Ph | 4-SO2CH3-Ph |
| 377 | 4-Cl—Ph | 4-OH—Ph |
| 378 | 4-Cl—Ph | 4-CH2OH—Ph |
| 379 | 4-Cl—Ph | 4-CHOHCH3-Ph |
| 380 | 4-Cl—Ph | 4-COH(CH3)2-Ph |
| 381 | 4-Cl—Ph | 4-CH3-Ph |
| 382 | 4-Cl—Ph | 4-C2H5-Ph |
| 383 | 4-Cl—Ph | 4-iPr—Ph |
| 384 | 4-Cl—Ph | 4-tBu—Ph |
| 385 | 4-Cl—Ph | 4-Ph—Ph |
| 386 | 4-Cl—Ph | 4-CH2Ph—Ph |
| 387 | 4-Cl—Ph | 4-CH2CO2Me—Ph |
| 388 | 4-Cl—Ph | 4-(1-piperidinyl)-Ph |
| 389 | 4-Cl—Ph | 4-(1-pyrrolidinyl)-Ph |
| 390 | 4-Cl—Ph | 4-(2-imidazolyl)-Ph |
| 391 | 4-Cl—Ph | 4-(1-imidazolyl)-Ph |
| 392 | 4-Cl—Ph | 4-(2-thiazolyl)-Ph |
| 393 | 4-Cl—Ph | 4-(3-pyrazolyl)-Ph |
| 394 | 4-Cl—Ph | 4-(1-pyrazolyl)-Ph |
| 395 | 4-Cl—Ph | 4-(1-tetrazolyl)-Ph |
| 396 | 4-Cl—Ph | 4-(5-tetrazolyl)-Ph |
| 397 | 4-Cl—Ph | 4-(2-pyridyl)-Ph |
| 398 | 4-Cl—Ph | 4-(2-thienyl)-Ph |
| 399 | 4-Cl—Ph | 4-(2-furanyl)-Ph |
| 400 | 4-Cl—Ph | 2-CN—Ph |
| 401 | 4-Cl—Ph | 2-COCH3-Ph |
| 402 | 4-Cl—Ph | 2-CO2Me—Ph |
| 403 | 4-Cl—Ph | 2-CO2Et—Ph |
| 404 | 4-Cl—Ph | 2-CO2H—Ph |
| 405 | 4-Cl—Ph | 2-CONH2-Ph |
| 406 | 4-Cl—Ph | 2-CONHMe—Ph |
| 407 | 4-Cl—Ph | 2-F—Ph |
| 408 | 4-Cl—Ph | 2-Cl—Ph |
| 409 | 4-Cl—Ph | 2-Br—Ph |
| 410 | 4-Cl—Ph | 2-NO2-Ph |
| 411 | 4-Cl—Ph | 2-NH2-Ph |
| 412 | 4-Cl—Ph | 2-NHMe—Ph |
| 413 | 4-Cl—Ph | 2-NMe2-Ph |
| 414 | 4-Cl—Ph | 2-NHCOCH3-Ph |
| 415 | 4-Cl—Ph | 2-SO2NH2-Ph |
| 416 | 4-Cl—Ph | 2-SO2NHMe—Ph |
| 417 | 4-Cl—Ph | 2-CF3-Ph |
| 418 | 4-Cl—Ph | 2-OCH3-Ph |
| 419 | 4-Cl—Ph | 2-OPh—Ph |
| 420 | 4-Cl—Ph | 2-OCF3-Ph |
| 421 | 4-Cl—Ph | 2-SCH3-Ph |
| 422 | 4-Cl—Ph | 2-SOCH3-Ph |
| 423 | 4-Cl—Ph | 2-SO2CH3-Ph |
| 424 | 4-Cl—Ph | 2-OH—Ph |
| 425 | 4-Cl—Ph | 2-CH2OH—Ph |
| 426 | 4-Cl—Ph | 2-CHOHCH3-Ph |
| 427 | 4-Cl—Ph | 2-COH(CH3)2-Ph |
| 428 | 4-Cl—Ph | 2-CHOHPh—Ph |
| 429 | 4-Cl—Ph | 2-CH3-Ph |
| 430 | 4-Cl—Ph | 2-C2H5-Ph |
| 431 | 4-Cl—Ph | 2-iPr—Ph |
| 432 | 4-Cl—Ph | 2-tBu—Ph |
| 433 | 4-Cl—Ph | 2-Ph—Ph |
| 434 | 4-Cl—Ph | 2-CH2Ph—Ph |
| 435 | 4-Cl—Ph | 2-CH2CO2Me—Ph |
| 436 | 4-Cl—Ph | 2-(1-piperidinyl)-Ph |
| 437 | 4-Cl—Ph | 2-(1-pyrrolidinyl)-Ph |
| 438 | 4-Cl—Ph | 2-(2-imidazolyl)-Ph |
| 439 | 4-Cl—Ph | 2-(1-imidazolyl)-Ph |
| 440 | 4-Cl—Ph | 2-(2-thiazolyl)-Ph |
| 441 | 4-Cl—Ph | 2-(3-pyrazolyl)-Ph |
| 442 | 4-Cl—Ph | 2-(1-pyrazolyl)-Ph |
| 443 | 4-Cl—Ph | 2-(1-tetrazolyl)-Ph |
| 444 | 4-Cl—Ph | 2-(5-tetrazolyl)-Ph |
| 445 | 4-Cl—Ph | 2-(2-pyridyl)-Ph |
| 446 | 4-Cl—Ph | 2-(2-thienyl)-Ph |
| 447 | 4-Cl—Ph | 2-(2-furanyl)-Ph |
| 448 | 4-Cl—Ph | 2,4-diF—Ph |
| 449 | 4-Cl—Ph | 2,5-diF—Ph |
| 450 | 4-Cl—Ph | 2,6-diF—Ph |
| 451 | 4-Cl—Ph | 3,4-diF—Ph |
| 452 | 4-Cl—Ph | 3,5-diF—Ph |
| 453 | 4-Cl—Ph | 2,4-diCl—Ph |
| 454 | 4-Cl—Ph | 2,5-diCl—Ph |
| 455 | 4-Cl—Ph | 2,6-diCl—Ph |
| 456 | 4-Cl—Ph | 3,4-diCl—Ph |
| 457 | 4-Cl—Ph | 3,5-diCl—Ph |
| 458 | 4-Cl—Ph | 3,4-diCF3-Ph |
| 459 | 4-Cl—Ph | 3,5-diCF3-Ph |
| 460 | 4-Cl—Ph | 5-Cl-2-MeO—Ph |
| 461 | 4-Cl—Ph | 5-Cl-2-Me—Ph |
| 462 | 4-Cl—Ph | 2-F-5-Me—Ph |
| 463 | 4-Cl—Ph | 2-F-5-NO2-Ph |
| 464 | 4-Cl—Ph | 3,4-OCH2O—Ph |
| 465 | 4-Cl—Ph | 3,4-OCH2CH2O—Ph |
| 466 | 4-Cl—Ph | 2-MeO-4-Me—Ph |
| 467 | 4-Cl—Ph | 2-MeO-5-Me—Ph |
| 468 | 4-Cl—Ph | 1-naphthyl |
| 469 | 4-Cl—Ph | 2-naphthyl |
| 470 | 4-Cl—Ph | 2-thienyl |
| 471 | 4-Cl—Ph | 3-thienyl |
| 472 | 4-Cl—Ph | 2-furanyl |
| 473 | 4-Cl—Ph | 3-furanyl |
| 474 | 4-Cl—Ph | 2-pyridyl |
| 475 | 4-Cl—Ph | 3-pyridyl |
| 476 | 4-Cl—Ph | 4-pyridyl |
| 477 | 4-Cl—Ph | 2-indolyl |
| 478 | 4-Cl—Ph | 3-indolyl |
| 479 | 4-Cl—Ph | 5-indolyl |
| 480 | 4-Cl—Ph | 6-indolyl |
| 481 | 4-Cl—Ph | 3-indazolyl |
| 482 | 4-Cl—Ph | 5-indazolyl |
| 483 | 4-Cl—Ph | 6-indazolyl |
| 484 | 4-Cl—Ph | 2-imidazolyl |
| 485 | 4-Cl—Ph | 3-pyrazolyl |
| 486 | 4-Cl—Ph | 2-thiazolyl |
| 487 | 4-Cl—Ph | 5-tetrazolyl |
| 488 | 4-Cl—Ph | 2-benzimidazolyl |
| 489 | 4-Cl—Ph | 5-benzimidazolyl |
| 490 | 4-Cl—Ph | 2-benzothiazolyl |
| 491 | 4-Cl—Ph | 5-benzothiazolyl |
| 492 | 4-Cl—Ph | 2-benzoxazolyl |
| 493 | 4-Cl—Ph | 5-benzoxazolyl |
| 494 | 2-Cl—Ph | 3-CN—Ph |
| 495 | 2-Cl—Ph | 3-COCH3-Ph |
| 496 | 2-Cl—Ph | 3-CO2Me—Ph |
| 497 | 2-Cl—Ph | 3-CO2Et—Ph |
| 498 | 2-Cl—Ph | 3-CO2H—Ph |
| 499 | 2-Cl—Ph | 3-CONH2-Ph |
| 500 | 2-Cl—Ph | 3-F—Ph |
| 501 | 2-Cl—Ph | 3-Cl—Ph |
| 502 | 2-Cl—Ph | 3-NH2-Ph |
| 503 | 2-Cl—Ph | 3-SO2NH2-Ph |
| 504 | 2-Cl—Ph | 3-CF3-Ph |
| 505 | 2-Cl—Ph | 3-OCH3-Ph |
| 506 | 2-Cl—Ph | 3-OEt—Ph |
| 507 | 2-Cl—Ph | 3-OCF3-Ph |
| 508 | 2-Cl—Ph | 3-SO2CH3-Ph |
| 509 | 2-Cl—Ph | 3-OH—Ph |

TABLE 1-continued

| | | |
|---|---|---|
| 510 | 2-Cl—Ph | 3-CH3-Ph |
| 511 | 2-Cl—Ph | 3-C2H5-Ph |
| 512 | 2-Cl—Ph | 4-CN—Ph |
| 513 | 2-Cl—Ph | 4-COCH3-Ph |
| 514 | 2-Cl—Ph | 4-CO2Me—Ph |
| 515 | 2-Cl—Ph | 4-CO2Et—Ph |
| 516 | 2-Cl—Ph | 4-CO2H—Ph |
| 517 | 2-Cl—Ph | 4-CONH2-Ph |
| 518 | 2-Cl—Ph | 4-F—Ph |
| 519 | 2-Cl—Ph | 4-Cl—Ph |
| 520 | 2-Cl—Ph | 4-NH2-Ph |
| 521 | 2-Cl—Ph | 4-SO2NH2-Ph |
| 522 | 2-Cl—Ph | 4-CF3-Ph |
| 523 | 2-Cl—Ph | 4-OCH3-Ph |
| 524 | 2-Cl—Ph | 4-OEt—Ph |
| 525 | 2-Cl—Ph | 4-OCF3-Ph |
| 526 | 2-Cl—Ph | 4-SO2CH3-Ph |
| 527 | 2-Cl—Ph | 4-OH—Ph |
| 528 | 2-Cl—Ph | 4-CH3-Ph |
| 529 | 2-Cl—Ph | 4-C2H5-Ph |
| 530 | 2-Cl—Ph | 2,4-diF—Ph |
| 531 | 2-Cl—Ph | 2,5-diF—Ph |
| 532 | 2-Cl—Ph | 3,4-diF—Ph |
| 533 | 2-Cl—Ph | 3,5-diF—Ph |
| 534 | 2-Cl—Ph | 2,4-diCl—Ph |
| 535 | 2-Cl—Ph | 2,5-diCl—Ph |
| 536 | 2-Cl—Ph | 3,4-diCl—Ph |
| 537 | 2-Cl—Ph | 3,5-diCl—Ph |
| 538 | 2-Cl—Ph | 3,4-OCH2O—Ph |
| 539 | 2-Cl—Ph | 3,4-OCH2CH2O—Ph |
| 540 | 2-Cl—Ph | 2-thienyl |
| 541 | 2-Cl—Ph | 2-furanyl |
| 542 | 2-Cl—Ph | 2-pyridyl |
| 543 | 2-Cl—Ph | 4-pyridyl |
| 544 | 2-Cl—Ph | 2-imidazolyl |
| 545 | 2-Cl—Ph | 3-pyrazolyl |
| 546 | 2-Cl—Ph | 2-thiazolyl |
| 547 | 2-Cl—Ph | 5-tetrazolyl |
| 548 | 2,4-diCl—Ph | 3-CN—Ph |
| 549 | 2,4-diCl—Ph | 3-COCH3-Ph |
| 550 | 2,4-diCl—Ph | 3-CO2Me—Ph |
| 551 | 2,4-diCl—Ph | 3-CO2Et—Ph |
| 552 | 2,4-diCl—Ph | 3-CO2H—Ph |
| 553 | 2,4-diCl—Ph | 3-CONH2-Ph |
| 554 | 2,4-diCl—Ph | 3-F—Ph |
| 555 | 2,4-diCl—Ph | 3-Cl—Ph |
| 556 | 2,4-diCl—Ph | 3-NH2-Ph |
| 557 | 2,4-diCl—Ph | 3-SO2NH2-Ph |
| 558 | 2,4-diCl—Ph | 3-CF3-Ph |
| 559 | 2,4-diCl—Ph | 3-OCH3-Ph |
| 560 | 2,4-diCl—Ph | 3-OEt—Ph |
| 561 | 2,4-diCl—Ph | 3-OCF3-Ph |
| 562 | 2,4-diCl—Ph | 3-SO2CH3-Ph |
| 563 | 2,4-diCl—Ph | 3-OH—Ph |
| 564 | 2,4-diCl—Ph | 3-CH3-Ph |
| 565 | 2,4-diCl—Ph | 3-C2H5-Ph |
| 566 | 2,4-diCl—Ph | 4-CN—Ph |
| 567 | 2,4-diCl—Ph | 4-COCH3-Ph |
| 568 | 2,4-diCl—Ph | 4-CO2Me—Ph |
| 569 | 2,4-diCl—Ph | 4-CO2Et—Ph |
| 570 | 2,4-diCl—Ph | 4-CO2H—Ph |
| 571 | 2,4-diCl—Ph | 4-CONH2-Ph |
| 572 | 2,4-diCl—Ph | 4-F—Ph |
| 573 | 2,4-diCl—Ph | 4-Cl—Ph |
| 574 | 2,4-diCl—Ph | 4-NH2-Ph |
| 575 | 2,4-diCl—Ph | 4-SO2NH2-Ph |
| 576 | 2,4-diCl—Ph | 4-CF3-Ph |
| 577 | 2,4-diCl—Ph | 4-OCH3-Ph |
| 578 | 2,4-diCl—Ph | 4-OEt—Ph |
| 579 | 2,4-diCl—Ph | 4-OCF3-Ph |
| 580 | 2,4-diCl—Ph | 4-SO2CH3-Ph |
| 581 | 2,4-diCl—Ph | 4-OH—Ph |
| 582 | 2,4-diCl—Ph | 4-CH3-Ph |
| 583 | 2,4-diCl—Ph | 4-C2H5-Ph |
| 584 | 2,4-diCl—Ph | 2,4-diF—Ph |
| 585 | 2,4-diCl—Ph | 2,5-diF—Ph |
| 586 | 2,4-diCl—Ph | 3,4-diF—Ph |
| 587 | 2,4-diCl—Ph | 3,5-diF—Ph |
| 588 | 2,4-diCl—Ph | 2,4-diCl—Ph |
| 589 | 2,4-diCl—Ph | 2,5-diCl—Ph |
| 590 | 2,4-diCl—Ph | 3,4-diCl—Ph |
| 591 | 2,4-diCl—Ph | 3,5-diCl—Ph |
| 592 | 2,4-diCl—Ph | 3,4-OCH2O—Ph |
| 593 | 2,4-diCl—Ph | 3,4-OCH2CH2O—Ph |
| 594 | 2,4-diCl—Ph | 2-thienyl |
| 595 | 2,4-diCl—Ph | 2-furanyl |
| 596 | 2,4-diCl—Ph | 2-pyridyl |
| 597 | 2,4-diCl—Ph | 4-pyridyl |
| 598 | 2,4-diCl—Ph | 2-imidazolyl |
| 599 | 2,4-diCl—Ph | 3-pyrazolyl |
| 600 | 2,4-diCl—Ph | 2-thiazolyl |
| 601 | 2,4-diCl—Ph | 5-tetrazolyl |
| 602 | 3-OCH3-Ph | 3-CN—Ph |
| 603 | 3-OCH3-Ph | 3-COCH3-Ph |
| 604 | 3-OCH3-Ph | 3-CO2Me—Ph |
| 605 | 3-OCH3-Ph | 3-CO2Et—Ph |
| 606 | 3-OCH3-Ph | 3-CO2H—Ph |
| 607 | 3-OCH3-Ph | 3-CONH2-Ph |
| 608 | 3-OCH3-Ph | 3-F—Ph |
| 609 | 3-OCH3-Ph | 3-Cl—Ph |
| 610 | 3-OCH3-Ph | 3-NH2-Ph |
| 611 | 3-OCH3-Ph | 3-SO2NH2-Ph |
| 612 | 3-OCH3-Ph | 3-CF3-Ph |
| 613 | 3-OCH3-Ph | 3-OCH3-Ph |
| 614 | 3-OCH3-Ph | 3-OEt—Ph |
| 615 | 3-OCH3-Ph | 3-OCF3-Ph |
| 616 | 3-OCH3-Ph | 3-SO2CH3-Ph |
| 617 | 3-OCH3-Ph | 3-OH—Ph |
| 618 | 3-OCH3-Ph | 3-CH3-Ph |
| 619 | 3-OCH3-Ph | 3-C2H5-Ph |
| 620 | 3-OCH3-Ph | 4-CN—Ph |
| 621 | 3-OCH3-Ph | 4-COCH3-Ph |
| 622 | 3-OCH3-Ph | 4-CO2Me—Ph |
| 623 | 3-OCH3-Ph | 4-CO2Et—Ph |
| 624 | 3-OCH3-Ph | 4-CO2H—Ph |
| 625 | 3-OCH3-Ph | 4-CONH2-Ph |
| 626 | 3-OCH3-Ph | 4-F—Ph |
| 627 | 3-OCH3-Ph | 4-Cl—Ph |
| 628 | 3-OCH3-Ph | 4-NH2-Ph |
| 629 | 3-OCH3-Ph | 4-SO2NH2-Ph |
| 630 | 3-OCH3-Ph | 4-CF3-Ph |
| 631 | 3-OCH3-Ph | 4-OCH3-Ph |
| 632 | 3-OCH3-Ph | 4-OEt—Ph |
| 633 | 3-OCH3-Ph | 4-OCF3-Ph |
| 634 | 3-OCH3-Ph | 4-SO2CH3-Ph |
| 635 | 3-OCH3-Ph | 4-OH—Ph |
| 636 | 3-OCH3-Ph | 4-CH3-Ph |
| 637 | 3-OCH3-Ph | 4-C2H5-Ph |
| 638 | 3-OCH3-Ph | 2,4-diF—Ph |
| 639 | 3-OCH3-Ph | 2,5-diF—Ph |
| 640 | 3-OCH3-Ph | 3,4-diF—Ph |
| 641 | 3-OCH3-Ph | 3,5-diF—Ph |
| 642 | 3-OCH3-Ph | 2,4-diCl—Ph |
| 643 | 3-OCH3-Ph | 2,5-diCl—Ph |
| 644 | 3-OCH3-Ph | 3,4-diCl—Ph |
| 645 | 3-OCH3-Ph | 3,5-diCl—Ph |
| 646 | 3-OCH3-Ph | 3,4-OCH2O—Ph |
| 647 | 3-OCH3-Ph | 3,4-OCH2CH2O—Ph |
| 648 | 3-OCH3-Ph | 2-thienyl |
| 649 | 3-OCH3-Ph | 2-furanyl |
| 650 | 3-OCH3-Ph | 2-pyridyl |
| 651 | 3-OCH3-Ph | 4-pyridyl |
| 652 | 3-OCH3-Ph | 2-imidazolyl |
| 653 | 3-OCH3-Ph | 3-pyrazolyl |
| 654 | 3-OCH3-Ph | 2-thiazolyl |
| 655 | 3-OCH3-Ph | 5-tetrazolyl |
| 656 | 2-F—Ph | 3,5-diCOCH3-Ph |
| 657 | 4-F—Ph | 3,5-diCOCH3-Ph |
| 658 | 2,4-diF—Ph | 3,5-diCOCH3-Ph |
| 659 | 2-Cl—Ph | 3,5-diCOCH3-Ph |
| 660 | 4-Cl-Ph | 3,5-diCOCH3-Ph |
| 661 | 2,4-diCl—Ph | 3,5-diCOCH3-Ph |
| 662 | 3-OCH3-Ph | 3,5-diCOCH3-Ph |

Utility

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437–2448 (1996) and Uguccioni et al., J. Clin. Invest., 100, 1137–1143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105–110 (1991), can be utilized in such assays. In particular, the compound of the present invention have activity in binding to the CCR-3 receptor in the aforementioned assays. As used herein, "activity" is intended to mean a compound demonstrating an IC50 of 10 µM or lower in concentration when measured in the aforementioned assays. Such a result is indicative of the intrinsic activity of the compounds as modulators of chemokine receptor activity. A general binding protocol is described below.

CCR3-Receptor Binding Protocol

Millipore filter plates (#MABVN1250) are treated with 5 µg/ml protamine in phosphate buffered saline, pH 7.2, for ten minutes at room temperature. Plates are washed three times with phosphate buffered saline and incubated with phosphate buffered saline for thirty minutes at room temperature. For binding, 50 µl of binding buffer (0.5% bovine serum albumen, 20 mM HEPES buffer and 5 mM magnesium chloride in RPMI 1640 media) with or without a test concentration of a compound present at a known concentration is combined with 50 µl of 125-I labeled human eotaxin (to give a final concentration of 150 pM radioligand) and 50 µl of cell suspension in binding buffer containing $5 \times 10^5$ total cells. Cells used for such binding assays can include cell lines transfected with a gene expressing CCR3 such as that described by Daugherty et al. (1996), isolated human eosinophils such as described by Hansel et al. (1991) or the AML14.3D10 cell line after differentiation with butyric acid as described by Tiffany et al. (1998). The mixture of compound, cells and radioligand are incubated at room temperature for thirty minutes. Plates are placed onto a vacuum manifold, vacuum applied, and plates washed three times with binding buffer with 0.5M NaCl added. The plastic skirt is removed from the plate, the plate allowed to air dry, the wells punch out and CPM counted. The percent inhibition of binding is calculated using the total count obtained in the absence of any competing compound or chemokine ligand and the background binding determined by addition of 100 nM eotaxin in place of the test compound.

The utility of the compounds in accordance with the present invention as inhibitors of the migration of eosinophils or cell lines expressing the chemokine receptors may be demonstrated by methodology known in the art, such as the chemotaxis assay disclosed by Bacon et al., Brit. J. Pharmacol., 95, 966–974 (1988). In particular, the compound of the present invention have activity in inhibition of the migration of eosinophils in the aforementioned assays. As used herein, "activity" is intended to mean a compound demonstrating an $IC_{50}$ of 10 µM or lower in concentration when measured in the aforementioned assays. Such a result is indicative of the intrinsic activity of the compounds as modulators of chemokine receptor activity. A human eosinophil chemotaxis assay protocol is described below.

Human Eosinophil Chemotaxis Assay

Neuroprobe MBA96 96-well chemotaxis chambers with Neuroprobe polyvinylpyrrolidone-free polycarbonate PFD5 5-micron filters in place are warmed in a 37° C. incubator prior to assay. Freshly isolated human eosinophils, isolated according to a method such as that described by Hansel et al. (1991), are suspended in RPMI 1640 with 0.1% bovine serum albumin at $1 \times 10^6$ cells/ml and warmed in a 37° C. incubator prior to assay. A 20 nM solution of human eotaxin in RPMI 1640 with 0.1% bovine serum albumin is warmed in a 37° C. incubator prior to assay. The eosinophil suspension and the 20 nM eotaxin solution are each mixed 1:1 with prewarmed RPMI 1640 with 0.1% bovine serum albumin with or without a dilution of a test compound that is at two fold the desired final concentration. These mixtures are warmed in a 37° C. incubator prior to assay. The filter is separated from the prewarmed Neuroprobe chemotaxis chamber and the eotaxin/compound mixture is placed into a Polyfiltronics MPC 96 well plate that has been placed in the bottom part of the Neuro Probe chemotaxis chamber. The approximate volume is 370 microliters and there should be a positive meniscus after dispensing. The filter is replaced above the 96 well plate, the rubber gasket is attached to the bottom of the upper chamber, and the chamber assembled. A 200 µl volume of the cell suspension/compound mixture is added to the appropriate wells of the upper chamber. The upper chamber is covered with a plate sealer, and the assembled unit placed in a 37° C. incubator for 45 minutes. After incubation, the plate sealer is removed and all remaining cell suspension is aspirated off. The chamber is disassembled and, while holding the filter by the sides at a 90-degree angle, unmigrated cells are washed away using a gentle stream of phosphate buffered saline dispensed from a squirt bottle and then the filter wiped with a rubber tipped squeegee. The filter is allowed to completely dry and immersed completely in Wright Giemsa stain for 30–45 seconds. The filter is rinsed with distilled water for 7 minutes, rinsed once with water briefly, and allowed to dry. Migrated cells are enumerated by microscopy.

Mammalian chemokine receptors provide a target for interfering with or promoting immune cell function in a mammal, such as a human. Compounds that inhibit or promote chemokine receptor function are particularly useful for modulating immune cell function for therapeutic purposes. Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays. As used herein, "activity" is intended to mean a compound demonstrating an IC50 of 10 μM or lower in concentration when measured in the aforementioned assays. Such a result is also indicative of the intrinsic activity of the compounds as modulators of chemokine receptor activity.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as brompheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal antiinflammatory agents (NSAIDS) such as propionic acid derivatives (alminoprofen, benxaprofen, bucloxic acid, carprofen, fenbufen, fenoprofen, flurprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (l) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, antimetabolites such as azathioprine and 6-mercaptopurine, and cytotoxic cancer chemotherapeutic agents. The weight ratio of the compound of the present invention to the second active ingredient may be varied and will depend upon the effective doses of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenyl, polyhydroxyethylaspartamidephenyl, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula (I):

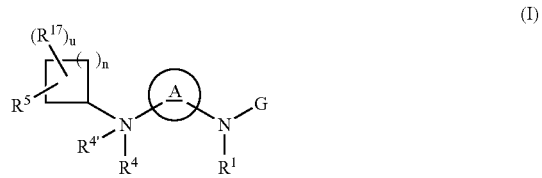

or stereoisomers or pharmaceutically acceptable salts thereof, wherein:

A is

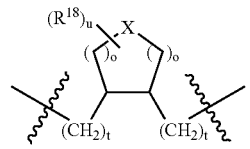

G is selected from —C(O)R$^3$, —C(O)NR$^2$R$^3$, —C(O)OR$^3$, —SO$_2$NR$^2$R$^3$, —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, and C(=C)(CN)$_2$)NR$^2$R$^3$;

W, at each occurrence, is independently selected from C or N, provided at least two of W are C;

X is NR$^{19}$;

X$^1$ and X$^2$ are independently selected from C and N;

Z$^1$ is selected from C and N;

Z$^2$ is selected from NR$^{1a}$, O, S and C;

R$^1$ and R$^2$ are independently selected from H, C$_{1-8}$ alkyl, C$_{3-8}$ alkenyl, C$_{3-8}$ alkynyl, and a (CH$_2$)$_r$—C$_{3-10}$ carbocyclic residue substituted with 0–5 R$^a$;

R$^{1a}$ is independently selected from H, C$_{1-6}$ alkyl, (CH$_2$)$_r$C$_{3-6}$ cycloalkyl, and a (CH$_2$)$_r$—C$_{3-10}$ carbocyclic residue substituted with 0–5 R$_a$;

R$^a$, at each occurrence, is selected from C$_{1-4}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^b$R$^b$, (CH$_2$)$_r$OH, (CH$_2$)$_r$OR$^c$, (CH$_2$)$_r$SH, (CH$_2$)$_r$SR$^c$, (CH$_2$)$_r$C(O)R$^b$, (CH$_2$)$_r$C(O)NR$^b$R$^b$, (CH$_2$)$_r$NR$^b$C(O)R$^c$, (CH$_2$)$_r$C(O)OR$^b$, (CH$_2$)$_r$OC(O)R$^c$, (CH$_2$)$_r$CH(=NR$^b$)NR$^b$R$^b$, (CH$_2$)$_r$NHC(=NR$^b$)NR$^b$R$^b$, (CH$_2$)$_r$S(O)$_p$R$^c$, (CH$_2$)$_r$S(O)$_2$NR$^b$R$^b$, (CH$_2$)$_r$NR$^b$S(O)$_2$R$^c$, and (CH$_2$)$_r$phenyl;

R$^b$, at each occurrence, is selected from H, C$_{1-6}$ alkyl, C$_{3-6}$ cycloalkyl, and phenyl;

R$^c$, at each occurrence, is selected from C$_{1-6}$ alkyl, C$_{3-6}$ cycloalkyl, and phenyl;

alternatively, R$^2$ and R$^3$ join to form a 5, 6, or 7-membered ring substituted with 0—3 R$^a$;

R$^3$ is selected from a (CR$^3$'R$^{3''}$)$_r$—C$_{3-10}$ carbocyclic residue substituted with 0–5 R$^{15}$ and a (CR$^3$'R$^{3''}$)$_r$—5–10 membered heterocyclic system containing 1–4 heteroatoms selected from N, O, and S, substituted with 0–3 R$^{15}$;

R$^{3'}$ and R$^{3''}$, at each occurrence, are selected from H, C$_{1-6}$ alkyl, (CH$_2$)$_r$C$_{3-6}$ cycloalkyl, and phenyl;

R$^4$ is hydrogen, C$_{1-8}$ alkyl, C$_{2-8}$ alkenyl, C$_{2-8}$ alkynyl, (CH$_2$)$_r$C$_{3-6}$ cycloalkyl, and a (CH$_2$)$_r$—C$_{3-10}$ carbocyclic residue substituted with 0–5 R$^a$;

alternatively, R$^4$ joins with R$^8$ or R$^{11}$ to form a pyrrolidine or piperidine ring system substituted with 0–3 R$^{4d}$;

R$^{4'}$ is absent, taken with the nitrogen to which it is attached to form an N-oxide, or selected from C$_{1-8}$ alkyl, C$_{2-8}$ alkenyl, C$_{3-8}$ alkynyl, (CH$_2$)$_q$C$_{3-6}$ cycloalkyl, (CH$_2$)$_q$C(O)R$^{4b}$, (CH$_2$)$_q$C(O)NR$^{4a}$R$^{4a'}$, (CH$_2$)$_q$C(O)OR$^{4a}$, and a (CH$_2$)$_r$—C$_{3-10}$ carbocyclic residue substituted with 0–3 R$^{4c}$;

R$^{4a}$ and R$^{4a'}$, at each occurrence, are selected from H, C$_{1-6}$ alkyl, (CH$_2$)$_r$C$_{3-6}$ cycloalkyl, and phenyl;

R$^{4b}$, at each occurrence, is selected from C$_{1-6}$ alkyl, C$_{2-8}$ alkenyl, (CH$_2$)$_r$C$_{3-6}$ cycloalkyl, C$_{2-8}$ alkynyl, and phenyl;

R$^{4c}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, (CH$_2$)$_r$OH, (CH$_2$)$_r$SC$_{1-5}$ alkyl, (CH$_2$)$_r$NR$^{4a}$R$^{4a'}$, and (CH$_2$)$_r$phenyl;

R$^{4d}$, is selected from H, C$_{1-6}$ alkyl, (CHR')$_q$OH, (CHR')$_q$OR$^{7a}$, (CHR')$_q$OC(O)R$^{7b}$, (CHR')$_q$OC(O)NHR$^{7a}$;

R$^5$ is selected from a (CR$^5$R$^{5''}$)$_b$—C$_{3-10}$ carbocyclic residue substituted with 0–5 R$^{16}$ and a (CR$^5$R$^{5''}$) t-5–10 membered heterocyclic system containing 1–4 heteroatoms selected from N, O, and S, substituted with 0–3 R$^{16}$;

R$^{5'}$ and R$^{5''}$, at each occurrence, are selected from H, C$_{1-6}$ alkyl, (CH$_2$)$_r$C$_{3-6}$ cycloalkyl, and phenyl;

R$^{15}$, at each occurrence, is selected from C$_{1-8}$ alkyl, (CH$_2$)$_r$C$_{3-6}$ cycloalkyl, Cl, Br, I, F, NO$_2$, CN, (CHR')$_r$NR$^{15a}$R$^{15a'}$, (CHR')$_r$OH, (CHR')$_r$O(CHR')$_r$R$^{15d}$, (CHR')$_r$SH, (CHR')$_r$C(O)H, (CHR')$_r$S(CHR')$_r$R$^{15d}$, (CHR')$_r$C(O)OH, (CHR')$_r$C(O)(CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15a}$R$^{15a'}$, (CHR')$_r$C(O)O(CHR')$_r$R$^{15d}$, (CHR')$_r$OC(O)(CHR')$_r$R$^{15b}$, (CHR')$_r$C(=NR$^{15f}$)NR$^{15a}$R$^{15a'}$, (CHR')$_r$NHC(=NR$^{15f}$)NR$^{15a}$R$^{15a'}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is selected from H, C$_{1-6}$ alkyl, C$_{2-8}$ alkenyl, C$_{2-8}$ alkynyl, (CH$_2$)$_q$C$_{3-6}$ cycloalkyl, and (CH$_2$)$_r$phenyl substituted with R$^{15e}$;

R$^{15a}$ and R$^{15a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{15e}$, and a (CH$_2$)$_r$-5–10 membered heterocyclic system containing 1–4 heteroatoms selected from N, O, and S, substituted with 0–2 R$^{15e}$;

R$^{15b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–3 R$^{15e}$, and (CH$_2$)$_r$-5–6 membered heterocyclic system containing 1–4 heteroatoms selected from N, O, and S, substituted with 0–2 R$^{15e}$;

R$^{15d}$, at each occurrence, is selected from C$_{3-8}$ alkenyl, C$_{3-8}$ alkynyl, methyl, CF$_3$, C$_{2-6}$ alkyl substituted with 0–3 R$^{15e}$, a (CH$_2$)$_r$—C$_{3-10}$ carbocyclic residue substituted with 0–3 R$^{15e}$, and a (CH$_2$)$_r$-5–6 membered heterocyclic system containing 1–4 heteroatoms selected from N, O, and S, substituted with 0–3 R$^{15e}$;

R$^{15e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{15f}$R$^{15f'}$, and (CH$_2$)$_r$phenyl;

R$^{15f}$, at each occurrence, is selected from H, C$_{1-6}$ alkyl, C$_{3-6}$ cycloalkyl, and phenyl;

R$^{16}$, at each occurrence, is selected from C$_{1-8}$ alkyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$SH, (CHR')$_r$C(O)H, (CHR')$_r$S(CHR')$_r$R$^{16d}$, (CHR')$_r$C(O)OH, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$C(O)O(CHR')$_r$R$^{16d}$, (CHR')$_r$OC(O)(CHR')$_r$R$^{16b}$, (CHR')$_r$C(=NR$^{16f}$)NR$^{16a}$R$^{16a'}$, (CHR')$_r$NHC(=NR$^{16f}$)NR$^{16a}$R$^{16a'}$, (CHR')$_r$S(O)$_p$(CHR')$_r$R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, C$_{2-8}$ alkenyl substituted with 0–3 R', C$_{2-8}$ alkynyl substituted with 0–3 R', and (CHR')$_r$phenyl substituted with 0–3 R$^{16e}$;

R$^{16a}$ and R$^{16a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{16e}$, and a (CH$_2$)$_r$-5–10 membered heterocyclic system containing 1–4 heteroatoms selected from N, O, and S, substituted with 0–2 R$^{16e}$;

R$^{16b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0–3 R$^{16e}$, and a (CH$_2$)$_r$-5–6 membered heterocyclic system containing 1–4 heteroatoms selected from N, O, and S, substituted with 0–2 R$^{16e}$;

R$^{16d}$, at each occurrence, is selected from C$_{3-8}$ alkenyl, C$_{3-8}$ alkynyl, methyl, CF$_3$, C$_{2-6}$ alkyl substituted with 0–3 R$^{16e'}$, a (CH$_2$)$_r$—C$_{3-10}$ carbocyclic residue substituted with 0–3 R$^{16e}$, and a (CH$_2$)$_r$-5–6 membered heterocyclic system containing 1–4 heteroatoms selected from N, O, and S, substituted with 0–3 R$^{16e}$;

R$^{16e}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{16f}$R$^{16f'}$, and (CH$_2$)$_r$phenyl;

R$^{16f}$, at each occurrence, is selected from H, C$_{1-5}$ alkyl, and C$_{3-6}$ cycloalkyl, and phenyl;

R$^{17}$, is selected from H, C$_{1-6}$ alkyl, C$_{2-8}$ alkenyl, C$_{2-8}$ alkynyl, (CH$_2$)$_q$OH, (CH$_2$)$_q$SH, (CH$_2$)$_q$OR$^{17d}$, (CH$_2$)$_q$SR$^{17d}$, (CH$_2$)$_q$NR$^{17a}$R$^{17a'}$, (CH$_2$)$_q$C(O)OH, (CH$_2$)$_q$C(O)R$^{17b}$, (CH$_2$)$_q$C(O)NR$^{17a}$R$^{17a'}$, (CH$_2$)$_q$NR$^{17a}$C(O)R$^{17b}$, (CH$_2$)$_q$NR$^{17a}$C(O)H, (CH$_2$)$_q$C(O)OR$^{17a}$, (CH$_2$)$_q$OC(O)R$^{17b}$, (CH$_2$)$_q$S(O)$_p$R$^{17b}$, (CH$_2$)$_q$S(O)$_2$NR$^{17a}$R$^{17a'}$, (CH$_2$)$_q$NR$^{17a}$S(O)$_2$R$^{17b}$, C$_{1-6}$ haloalkyl, a (CH$_2$)$_r$—C$_{3-10}$ carbocyclic residue substituted with 0–3 R$^{17c}$, and a (CH$_2$)$_r$-5–10 membered heterocyclic system containing 1–4 heteroatoms selected from N, O, and S, substituted with 0–2 R$^{17c}$;

R$^{17a}$ and R$^{17a'}$, at each occurrence, are selected from H, C$_{1-6}$ alkyl, C$_{3-8}$ alkenyl, C$_{3-8}$ alkynyl, a (CH$_2$)$_r$—C$_{3-10}$ carbocyclic residue substituted with 0–5 R$^{17e}$, and a (CH$_2$)$_r$-5–10 membered heterocyclic system containing 1–4 heteroatoms selected from N, O, and S, substituted with 0–3 R$^{17e}$;

R$^{17b}$, at each occurrence, is selected from C$_{1-6}$ alkyl, C$_{2-8}$ alkenyl, C$_{2-8}$ alkynyl, a (CH$_2$)$_r$C$_{3-6}$ carbocyclic residue substituted with 0–2 R$^{17e}$, and a (CH$_2$)$_r$-5–6 membered heterocyclic system containing 1–4 heteroatoms selected from N, O, and S, substituted with 0–3 R$^{17e}$;

R$^{17c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{17f}$R$^{17f'}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{17b}$, (CH$_2$)$_r$C(O)NR$^{17f}$R$^{17f}$, (CH$_2$)$_r$NR$^{17f}$C(O)R$^{17a}$, (CH$_2$)$_r$C(O)OC$_{1-4}$ alkyl, (CH$_2$)$_r$OC(O)R$^{17b}$, (CH$_2$)$_r$C(=NR$^{17f}$)NR$^{17f}$R$^{17f}$, (CH$_2$)$_r$S(O)$_p$R$^{17b}$, (CH$_2$)$_r$NHC(=NR$^{17f}$)NR$^{17f}$R$^{17f}$, (CH$_2$)$_r$S(O)$_2$NR$^{17f}$R$^{17f}$, (CH$_2$)$_r$NR$^{17f}$S(O)$_2$R$^{17b}$, and (CH$_2$)$_r$phenyl substituted with 0–3 R$^{17e}$;

R$^{17d}$, at each occurrence, is selected from methyl, CF$_3$, C$_{2-6}$ alkyl substituted with 0–3 R$^{17e}$, C$_{3-6}$ alkenyl, C$_{3-6}$ alkynyl, and a C$_{3-10}$ carbocyclic residue substituted with 0–3 R$^{17c}$;

R$^{17e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{17f}$R$^{17f}$, and (CH$_2$)$_r$phenyl;

R$^{17f}$, at each occurrence, is selected from H, C$_{1-6}$ alkyl, and C$_{3-6}$ cycloalkyl;

R$^{18}$, is selected from H, C$_{1-6}$ alkyl, C$_{2-8}$ alkenyl, C$_{2-8}$ alkynyl, (CHR')$_q$OH, (CHR')$_q$SH, (CHR')$_q$OR$^{18d}$, (CHR')$_q$SR$^{18d}$, (CHR')$_q$NR$^{18a}$R$^{18a'}$, (CHR')$_r$C(O)OH, (CHR')$_r$C(O)R$^{18b}$, (CHR')$_r$C(O)NR$^{18a}$R$^{18a'}$, (CHR')$_q$NR$^{18a}$C(O)R$^{18a}$, (CHR')$_q$NR$^{18a}$C(O)H, (CHR')$_r$C(O)OR$^{18a}$, (CHR')$_q$OC(O)R$^{18b}$, (CHR')$_q$S(O)$_p$R$^{18b}$, (CHR')$_q$S(O)$_2$NR$^{18a}$R$^{18a'}$, (CHR')$_q$NR$^{18a}$S(O)$_2$R$^{18b}$, C$_{1-6}$ haloalkyl, a (CHR')$_r$—C$_{3-10}$ carbocyclic residue substituted with 0–3 R$^{18c}$, and a (CHR')$_r$-5–10 membered heterocyclic system containing 1–4 heteroatoms selected from N, O, and S, substituted with 0–2 R$^{18c}$;

R$^{18a}$ and R$^{18a'}$, at each occurrence, are selected from H, C$_{1-6}$ alkyl, C$_{3-8}$ alkenyl, C$_{3-8}$ alkynyl, a (CH$_2$)$_r$C$_{3-10}$ carbocyclic residue substituted with 0–5 R$^{18e}$, and a (CH$_2$)$_r$-5–10 membered heterocyclic system containing 1–4 heteroatoms selected from N, O, and S, substituted with 0–3 R$^{18e}$;

R$^{18b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0–2 R$^{18e}$, and a (CH$_2$)$_r$-5–6 membered heterocyclic system containing 1–4 heteroatoms selected from N, O, and S, substituted with 0–3 R$^{18e}$;

R$^{18c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{18f}$R$^{18f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{18b}$, (CH$_2$)$_r$C(O)NR$^{18f}$R$^{18f}$, (CH$_2$)$_r$NR$^{18f}$C(O)R$^{18a}$, (CH$_2$)$_r$C(O)OC$_{1-4}$ alkyl, (CH$_2$)$_r$OC(O)R$^{18b}$, (CH$_2$)$_r$C(=NR$^{18f}$)NR$^{18f}$R$^{18f}$, (CH$_2$)$_r$S(O)$_p$R$^{18b}$, (CH$_2$)$_r$NHC(=NR$^{18f}$)NR$^{18f}$R$^{18f}$, (CH$_2$)$_r$S(O)$_2$NR$^{18f}$R$^{18f}$, (CH$_2$)$_r$NR$^{18f}$S(O)$_2$R$^{18b}$, and (CH$_2$)$_r$phenyl substituted with 0–3 R$^{18e}$;

R$^{18d}$, at each occurrence, is selected from methyl, CF$_3$, C$_{2-6}$ alkyl substituted with 0–3 R$^{18e}$, C$_{3-6}$ alkenyl, C$_{3-6}$ alkynyl, and a C$_{3-10}$ carbocyclic residue substituted with 0–3 R$^{18c}$;

R$^{18e}$, at each occurrence, is selected from C$_{1-6}$ alkyl, C$_{2-8}$ alkenyl, C$_{2-8}$ alkynyl, C$_{3-6}$ cycloalkyl, Cl, F, Br, I, CN, NO$_2$, (CF$_2$)$_r$CF$_3$, (CH$_2$)$_r$OC$_{1-5}$ alkyl, OH, SH, (CH$_2$)$_r$SC$_{1-5}$ alkyl, (CH$_2$)$_r$NR$^{18f}$R$^{18f}$, and (CH$_2$)$_r$phenyl;

R$^{18f}$, at each occurrence, is selected from H, C$_{1-6}$ alkyl, and C$_{3-6}$ cycloalkyl;

R$^{19}$ is selected from C$_{1-8}$ alkyl, C$_{3-8}$ alkenyl, C$_{3-8}$ alkynyl, —C(O)R$^{19b}$, —C(O)NR$^{19a}$R$^{19a}$, —C(O)OR$^{19a}$, and —SO$_2$R$^{19a}$, a (CHR')$_r$—C$_{3-10}$ carbocyclic residue substituted with 0–3 R$^{16}$, and a (CHR')$_r$-5–10 membered heterocyclic system containing 1–4 heteroatoms selected from N, O, and S, substituted with 0–2 R$^{16}$;

R$^{19a}$ is selected from C$_{1-8}$ alkyl, C$_{3-8}$ alkenyl, C$_{3-8}$ alkynyl, C$_{3-6}$ cycloalkyl, a (CR$^{5'}$R$^{5''}$)$_t$—C$_{3-10}$ carbocyclic residue substituted with 0–5 R$^{16}$ and a —(CR$^5$R$^{5''}$)$_r$-5–10 membered heterocyclic system containing 1–4 heteroatoms selected from N, O, and S, substituted with 0–3 R$^{16}$;

R$^{19b}$ is selected from H, C$_{1-8}$ alkyl, C$_{3-8}$ alkenyl, C$_{3-8}$ alkynyl, C$_{3-6}$ cycloalkyl, a (CR$^5$R$^{5''}$)$_t$—C$_{3-10}$ carbocyclic residue substituted with 0–5 R$^{16}$ and a (CR$^5$R$^{5''}$)$_r$-5–10 membered heterocyclic system containing 1–4 heteroatoms selected from N, O, and S, substituted with 0–3 R$^{16}$;

n, at each occurrence, is selected from 0, 1, 2, 3, 4, and 5;
o, at each occurrence, is selected from 1 and 2;
p, at each occurrence, is selected from 1 and 2;
r, at each occurrence, is selected from 0, 1, 2, 3, 4, and 5;
q, at each occurrence, is selected from 1, 2, 3, 4, and 5;
s, at each occurrence, is selected from 0, 1, and 2;
t, at each occurrence, is selected from 0, 1, 2, 3, 4, and 5; and
u, at each occurrence, is independently selected from 0, 1, and 2.

2. The compound of claim 1, wherein:
R$^{4'}$ is absent or, taken with the nitrogen to which it is attached to form an N-oxide.

3. The compound of claim 2, wherein:
A is t is selected from 0, 1, and 2.

4. The compound of claim 3, wherein:
R$^{17}$ is selected from H; and
R$^{18}$ is selected from H.

5. The compound of claim 4, wherein:
A is

6. The compound of claim 5, wherein:
G is selected from —C(O)R$^3$, —C(O)NR$^2$R$^3$, —C(O)OR$^3$, —SO$_2$NR$^2$R$^3$, and —SO$_2$R$^3$, —C(=S)NR$^2$R$^3$, C(=NR$^{1a}$)NR$^2$R$^3$, C(=CHCN)NR$^2$R$^3$, C(=CHNO$_2$)NR$^2$R$^3$, C(=C(CN)$_2$)NR$^2$R$^3$.

7. The compound of claim 6, wherein:
G is selected from —C(O)NR$^2$R$^3$, C(=NR$^{1a}$)NR$^2$R$^3$; C(=CHCN)NR$^2$R$^3$, C(=CHNO$_2$)NR$^2$R$^3$, and C(=C(CN)$_2$)NR$^2$R$^3$.

8. The compound of claim 7, wherein:
R$^{16}$, at each occurrence, is selected from methyl, ethyl, propyl, iso-propyl, C$_{2-8}$ alkenyl, C$_{2-8}$ alkynyl, (CH$_2$)$_r$C$_{3-6}$ cycloalkyl, Cl, Br, I, F, NO$_2$, CN, (CHR')$_r$NR$^{16a}$R$^{16a'}$, (CHR')$_r$OH, (CHR')$_r$O(CHR')$_r$R$^{16d}$, (CHR')$_r$C(O)(CHR')$_r$R$^{16b}$, (CHR')$_r$C(O)NR$^{16a}$R$^{16a'}$, (CHR')$_r$NR$^{16f}$C(O)(CHR')$_r$R$^{16b}$, (CHR')$_r$S(O)$_p$(CHR')$_r$ R$^{16b}$, (CHR')$_r$S(O)$_2$NR$^{16a}$R$^{16a'}$, (CHR')$_r$NR$^{16f}$S(O)$_2$(CHR')$_r$R$^{16b}$, C$_{1-6}$ haloalkyl, and (CHR')$_r$phenyl substituted with 0–3 R$^{16e}$;

R$^{16a}$ and R$^{16a'}$, at each occurrence, are selected from H, methyl, ethyl, and a (CH$_2$)$_r$—C$_{3-6}$ carbocyclic residue substituted with 0–2 R$^{16e}$;

R$^{16e}$, at each occurrence, is selected from methyl, ethyl, Cl, F, Br, I, CN, CF$_3$, and OCH$_3$;

R$^{16f}$, at each occurrence, is selected from H; and r is selected from 0, 1, and 2.

9. The compound of claim 8, wherein:

R$^3$ is selected from a (CR$^{3'}$R$^{3''}$)$_r$—C$_{3-6}$ carbocyclic residue substituted with 0–2 R$^{15}$ and a (CR$^{3'}$CR$^{3''}$)$_r$-5–10 membered heterocyclic system containing 1–4 heteroatoms selected from N, O, and S, subsituted with 0–2 R$^{15}$;

R$^{3'}$ and R$^{3'''}$, at each occurrence, are selected from H;

R$^{15}$, at each occurrence, is selected from C$_{1-8}$ alkyl, (CH$_2$)$_r$C$_{3-6}$ cycloalkyl, Cl, Br, F, CN, (CHR')$_r$NR$^{15a}$R$^{15a'}$, (CHR')$_r$OH, (CHR')$_r$O(CHR')$_r$R$^{15d}$, (CHR')$_r$C(O)(CHR')$_r$R$^{15b}$, (CHR')$_r$C(O)NR$^{15a}$R$^{15a'}$, (CHR')$_r$NR$^{15f}$C(O)(CHR')$_r$R$^{15b}$, (CHR')$_r$NR$^{15f}$C(O)NR$^{15f}$R$^{15f}$, (CHR')$_r$C(O)O(CHR')$_r$R$^{15d}$, (CHR')$_r$OC(O)(CHR')$_r$R$^{15b}$, (CHR')$_r$S(O)$_p$(CHR')$_r$R$^{15b}$, (CHR')$_r$S(O)$_2$NR$^{15a}$R$^{15a'}$, (CHR')$_r$NR$^{15f}$S(O)$_2$(CHR')$_r$R$^{15b}$, C$_{1-6}$ haloalkyl, C$_{2-8}$ alkenyl substituted with 0–3 R', C$_{2-8}$ alkynyl substituted with 0–3 R', (CHR')$_r$phenyl substituted with 0–3 R$^{15e}$, and a (CH$_2$)$_r$-5–10 membered heterocyclic system containing 1–4 heteroatoms selected from N, O, and S, substituted with 0–2 R$^{15e}$;

R', at each occurrence, is selected from H, and C$_{1-6}$ alkyl;

R$^{15a}$ and R$^{15a'}$, at each occurrence, are selected from H, C$_{1-6}$ alkyl, a (CH$_2$)$_r$—C$_{3-6}$ carbocyclic residue substituted with 0–5 R$^{15e}$, and a (CH$_2$)$_r$-5–6 membered heterocyclic system containing 1–2 heteroatoms selected from N, O, and S, substituted with 0–2 R$^{15e}$;

R$^{15b}$, at each occurrence, is selected from C$_{1-6}$ alkyl, a (CH$_2$)$_r$—C$_{3-6}$ carbocyclic residue substituted with 0–3 R$^{15e}$, and (CH$_2$)$_r$-5–6 membered heterocyclic system containing 1–2 heteroatoms selected from N, O, and S, substituted with 0–2 R$^{15e}$; and R$^{15e}$, at each occurrence, is selected from C$_{1-6}$ alkyl, Cl, F, Br, I, CN, (CF$_2$)$_r$CF$_3$, and OH.

10. The compound of claim 1 wherein the compound is selected from:

N-(3-acetylphenyl)-N'-({(2S) -1-[4-(4-fluorobenzyl)cyclohexyl]pyrrolidinyl}methyl)urea;

N-(3-acetylphenyl)-N'-({(2S) -1-[4-(4-fluorobenzyl)cyclohexyl]pyrrolidinyl}methyl)urea;

N-(3-acetylphenyl)-N'-({(2R)-1-[4-(4-fluorobenzyl)cyclohexyl]pyrrolidinyl}methyl)urea;

N-(3-acetylphenyl)-N'-({(2R)-1-[4-(4-fluorobenzyl)cyclohexyl]pyrrolidinyl}methyl)urea;

N-(3-acetylphenyl)-N'-{(3R)-1-[4-(4-fluorobenzyl)cyclohexyl]pyrrolidinyl}urea;

N-(3-acetylphenyl)-N'-{(3R)-1-[4-(4-fluorobenzyl)cyclohexyl]pyrrolidinyl}urea;

N-(3-acetylphenyl)-N'-{(3S)-1-[4-(4-fluorobenzyl)cyclohexyl]pyrrolidinyl}urea; and N-(3-acetylphenyl)-N'-{(3S) -1-[4-(4-fluorobenzyl)cyclohexyl]pyrrolidinyl}urea.

11. A pharmaceutical composition, comprising a pharmaceutically acceptable carrier and a therapeutically effective amount of a compound of claim 1.

12. A method for modulation of chemokine receptor activity comprising administering to a patient in need thereof a therapeutically effective amount of a compound of claim 1.

13. A method for treating or preventing inflammatory disease, comprising administering to a patient in need thereof a therapeutically effective amount of a compound of claim 1.

14. A method for treating or preventing asthma, comprising administering to a patient in need thereof a therapeutically effective amount of a compound of claim 1.

15. A pharmaceutical composition, comprising a pharmaceutically acceptable carrier and a therapeutically effective amount of a compound of claim 9.

16. A method for treating asthma, comprising administering to a patient in need thereof a therapeutically effective amount of a compound of claim 9.

* * * * *

UNITED STATES PATENT AND TRADEMARK OFFICE
CERTIFICATE OF CORRECTION

PATENT NO. : 7,126,010 B2  Page 1 of 1
APPLICATION NO. : 11/040585
DATED : October 24, 2006
INVENTOR(S) : Wacker et al.

It is certified that error appears in the above-identified patent and that said Letters Patent is hereby corrected as shown below:

In column 57, claim 1, line 23, please delete "$(CR^{5'}R^{5"})_b$" and insert

-- $(CR^{5'}R^{5"})_t$ --.

In column 57, claim 1, line 24, delete "$(CR^{5'}R^{5"})t\text{-}5\text{-}10$" and insert -- $(CR^{5'}R^{5"})_t\text{-}5\text{-}10$ --.

Signed and Sealed this

Fifteenth Day of April, 2008

JON W. DUDAS
*Director of the United States Patent and Trademark Office*